United States Patent
Huang

(10) Patent No.: US 7,612,635 B2
(45) Date of Patent: Nov. 3, 2009

(54) MEMS ACOUSTIC FILTER AND FABRICATION OF THE SAME

(75) Inventor: Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 245 days.

(21) Appl. No.: 11/462,333

(22) Filed: Aug. 3, 2006

(65) Prior Publication Data

US 2007/0046396 A1    Mar. 1, 2007

Related U.S. Application Data

(60) Provisional application No. 60/705,606, filed on Aug. 3, 2005.

(51) Int. Cl.
*H03H 9/00* (2006.01)
(52) U.S. Cl. ............... 333/186; 333/187; 333/193
(58) Field of Classification Search ......... 333/186–187, 333/193, 195, 201
See application file for complete search history.

(56) References Cited

U.S. PATENT DOCUMENTS

| 6,271,620 | B1 * | 8/2001 | Ladabaum | 310/334 |
| 2002/0041220 | A1 * | 4/2002 | Nguyen | 333/197 |

\* cited by examiner

*Primary Examiner*—Anh Q Tran
(74) *Attorney, Agent, or Firm*—Lee & Hayes, PLLC

(57) ABSTRACT

A MEMS acoustic filter has a MEMS resonator and at least two acoustic I/O ports to alter an input acoustic signal to an output acoustic signal. The first I/O port is adapted for interfacing with a medium, and the second I/O port for passing an acoustic signal to an acoustic transducer. Multiple MEMS resonators may be stacked to form a high order acoustic filter. An array of MEMS acoustic filters may be designed to function as an acoustic lens. The MEMS acoustic filter is particularly useful with an ultrasonic transducer, such as PZT and MUT. Fabrication methods to make the same are also disclosed.

34 Claims, 15 Drawing Sheets

| F 1 (-2α) | F 2 (-α) | F 3 (0) | F 4 (-α) | F 5 (-2α) |
|---|---|---|---|---|
| E 1 | E 2 | E 3 | E 4 | E 5 |
1100
FIG. 11
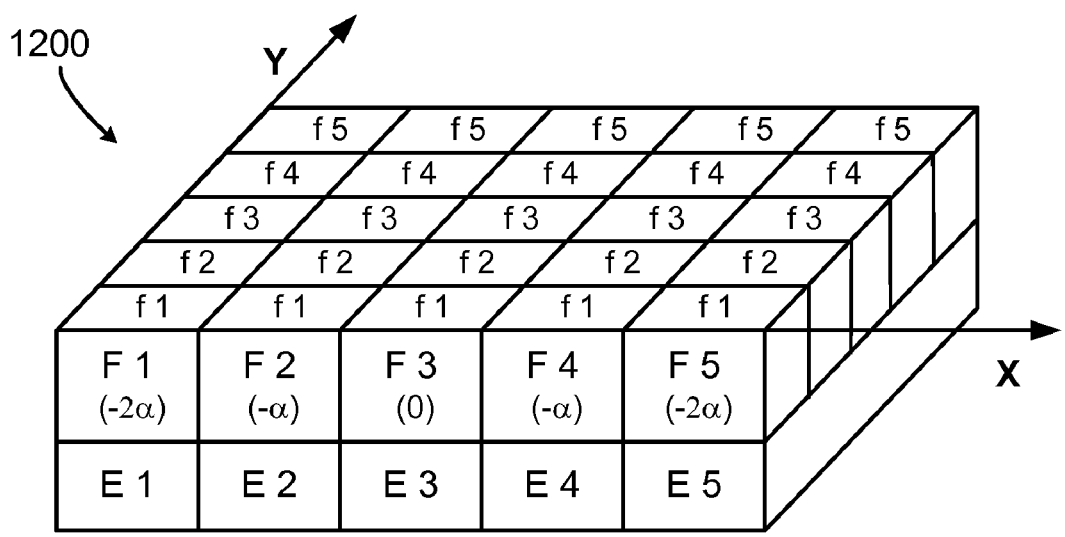
FIG. 12A
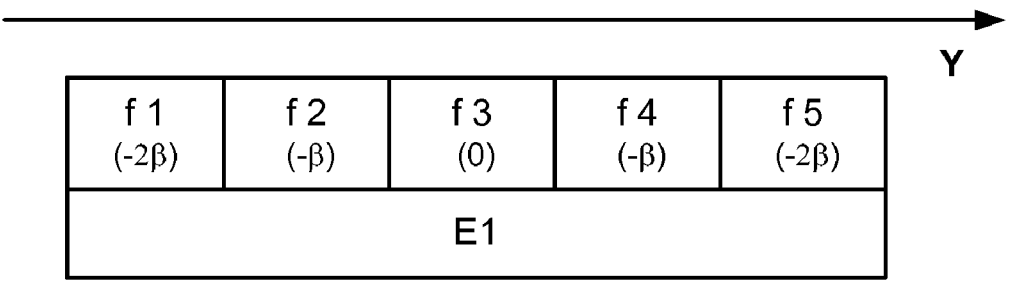
FIG. 12B

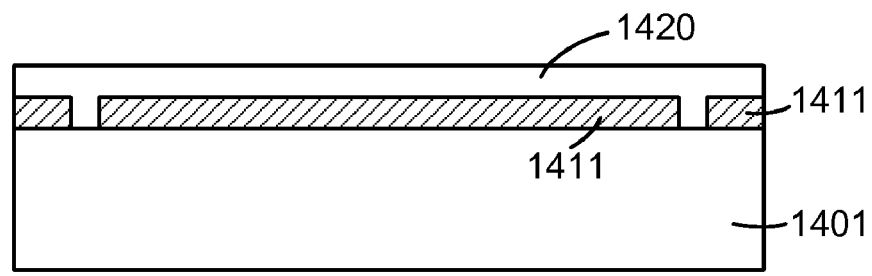
FIG. 14.1
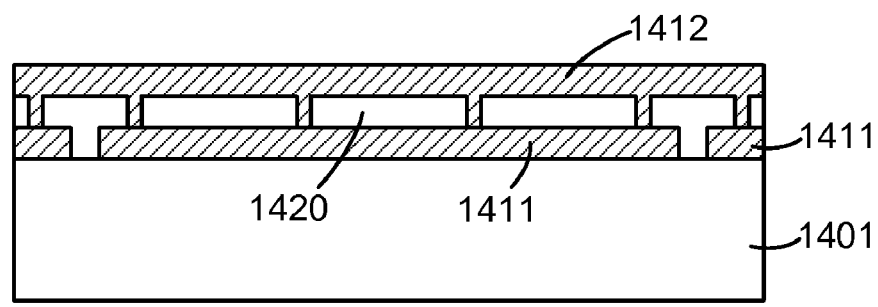
FIG. 14.2
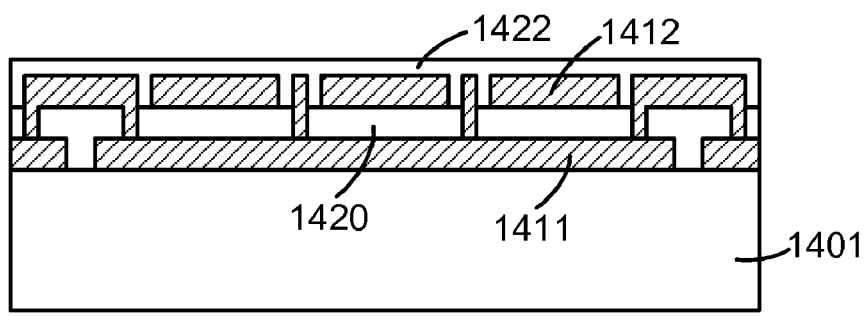
FIG. 14.3
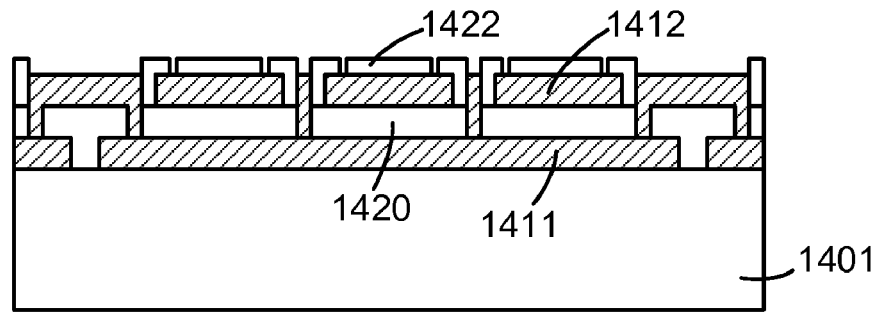
FIG. 14.4

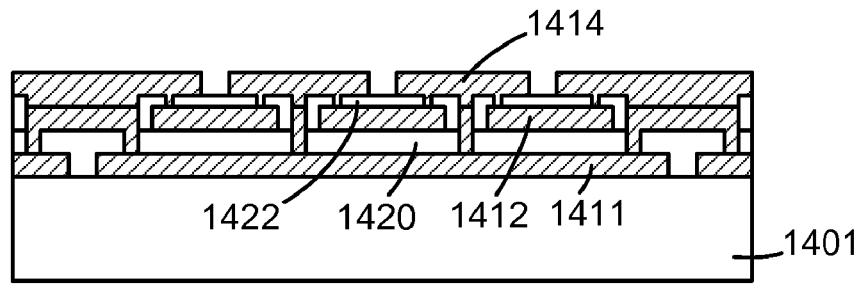
FIG. 14.5
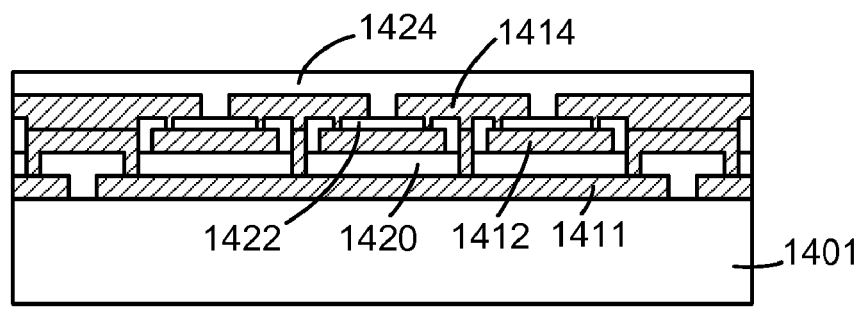
FIG. 14.6
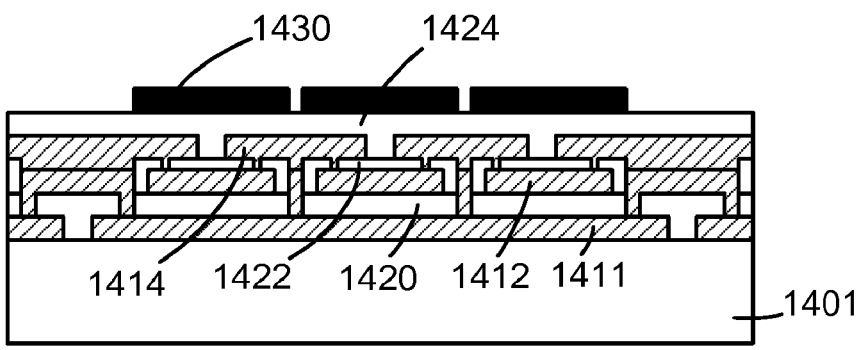
FIG. 14.7
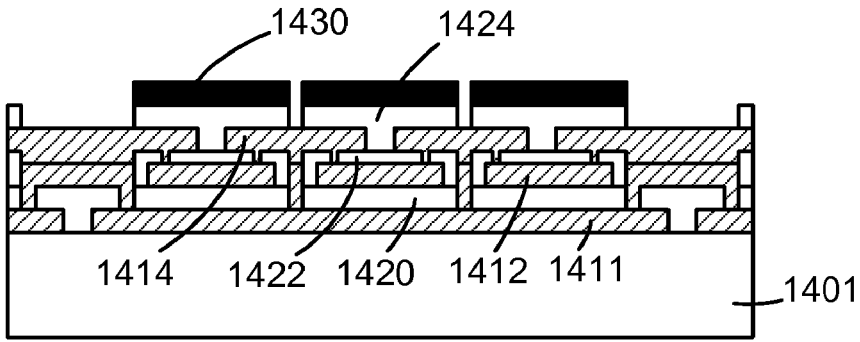
FIG. 14.8

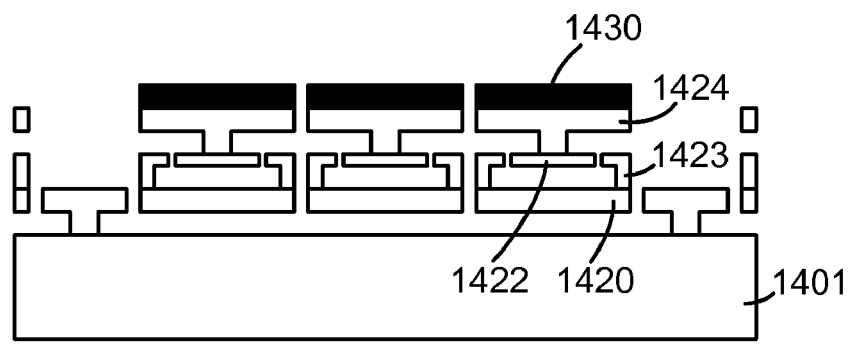
FIG. 14.9
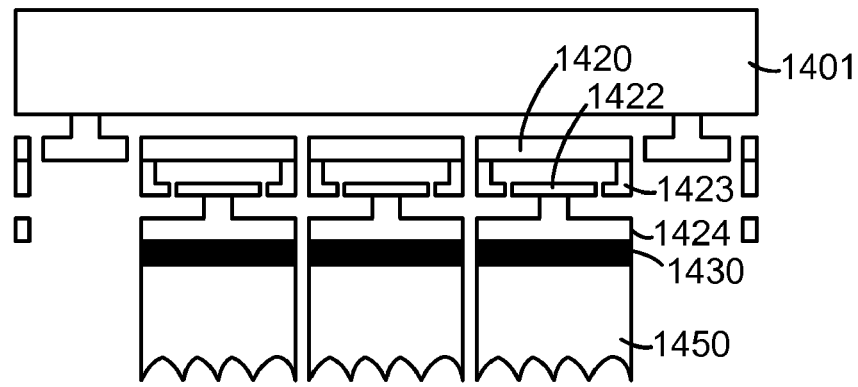
FIG. 14.10
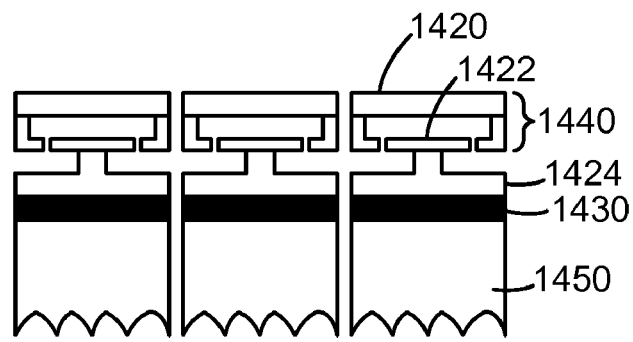
FIG. 14.11

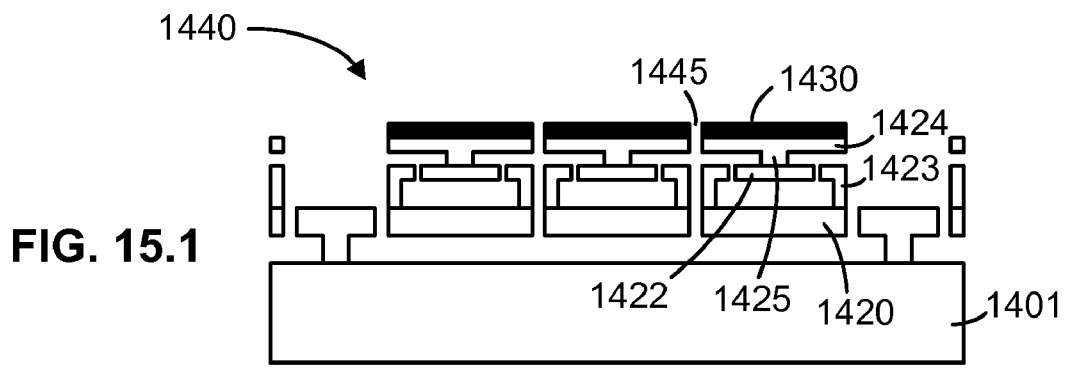
FIG. 15.1
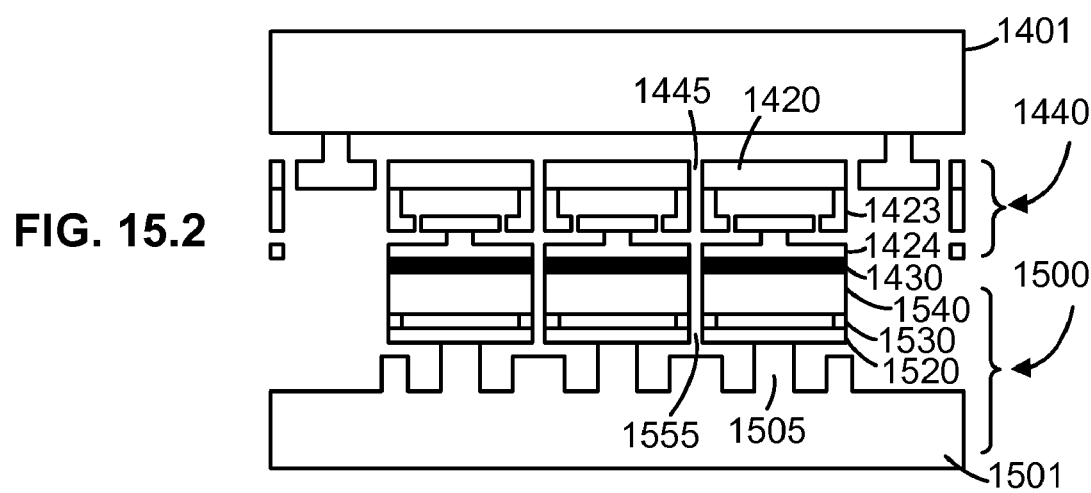
FIG. 15.2
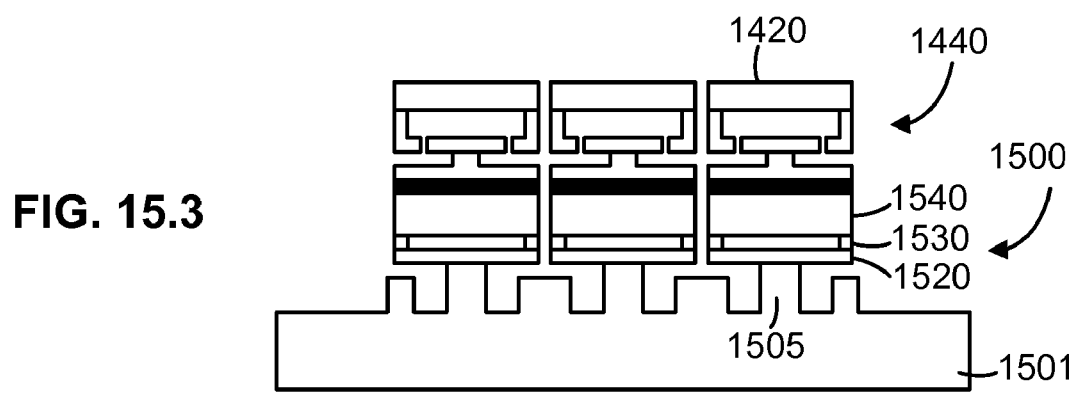
FIG. 15.3

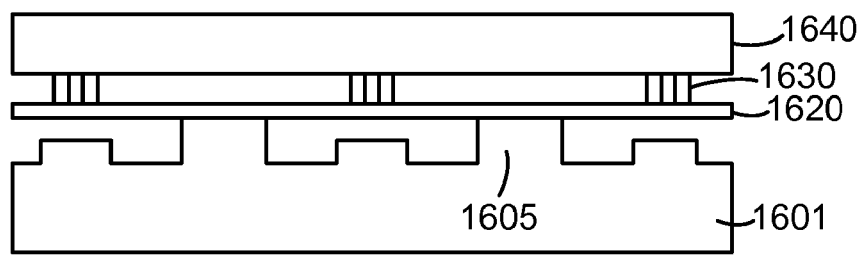
FIG. 16.1
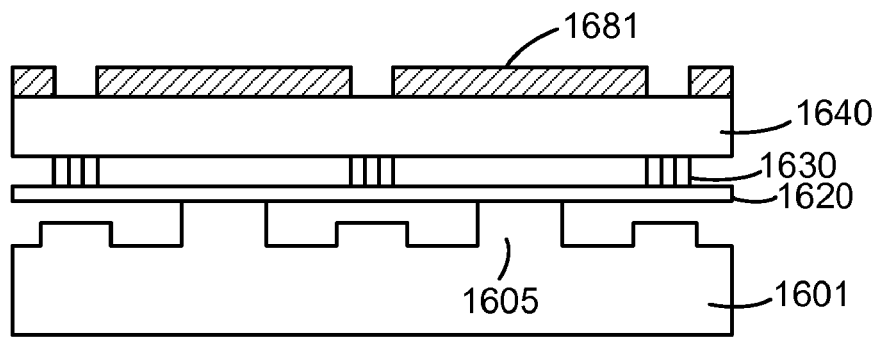
FIG. 16.2
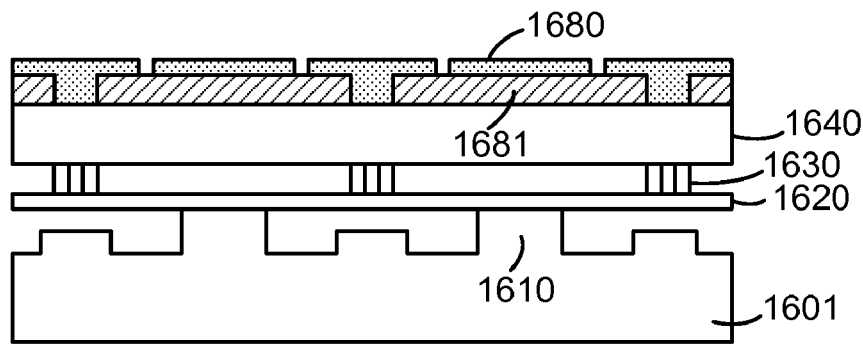
FIG. 16.3
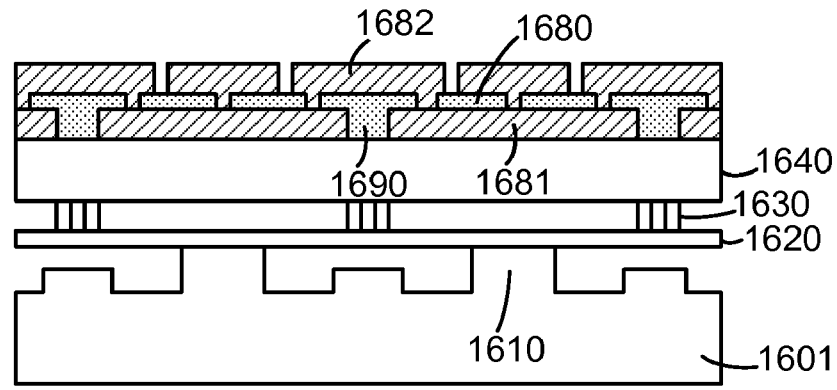
FIG. 16.4

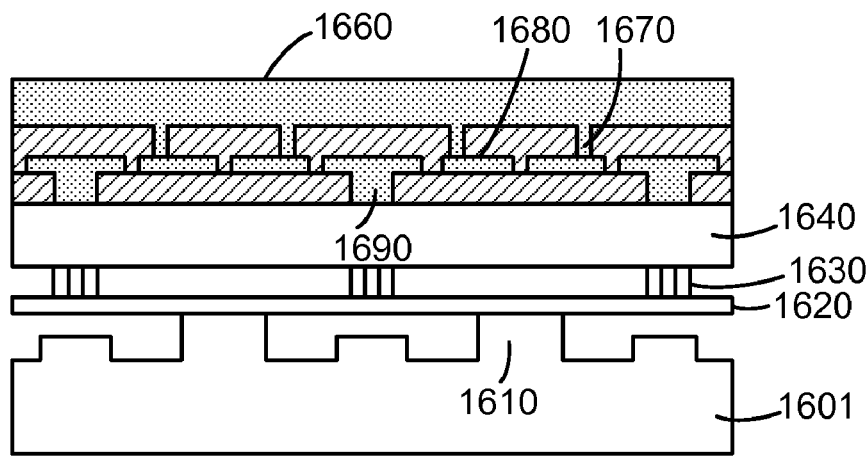
FIG. 16.5
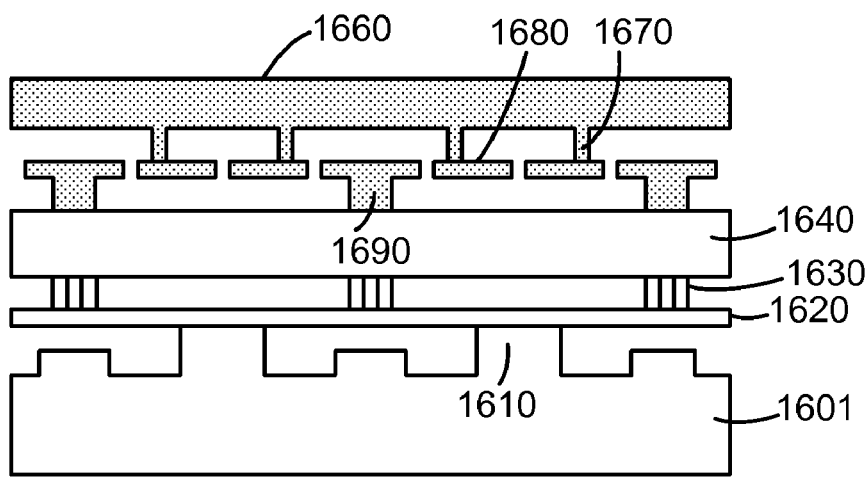
FIG. 16.6
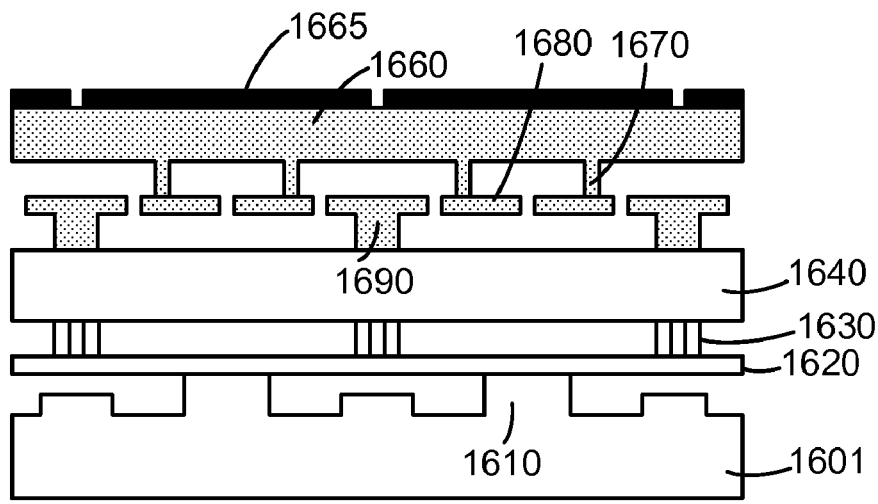
FIG. 16.7

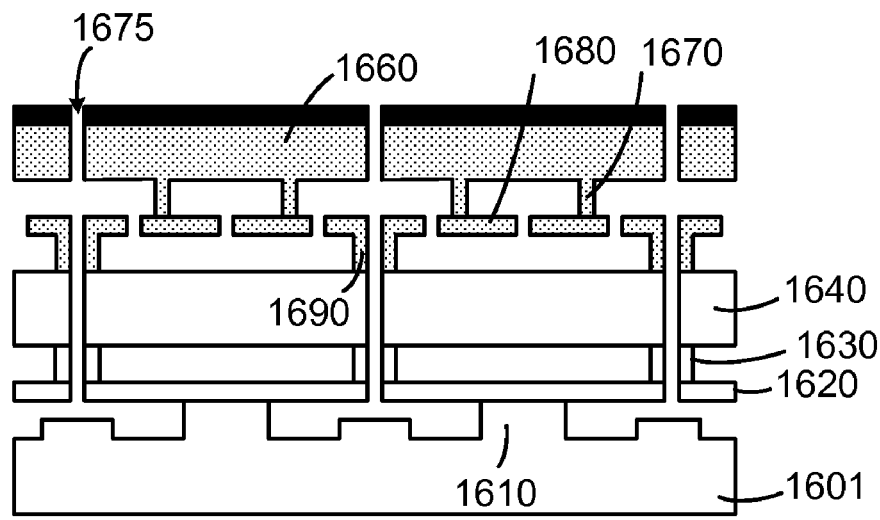
FIG. 16.8
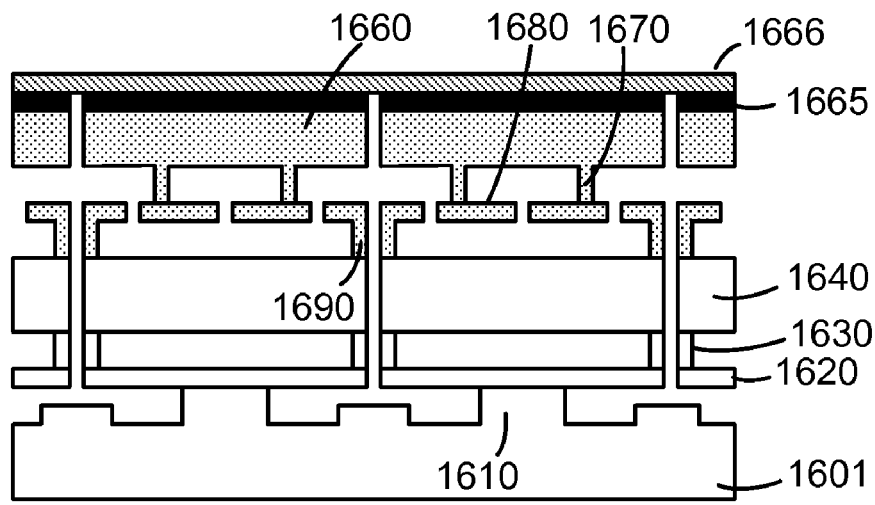
FIG. 16.9

MEMS ACOUSTIC FILTER AND FABRICATION OF THE SAME

PRIORITY

This application claims priority from U.S. Provisional Application Ser. No. 60/705,606, filed Aug. 3, 2005, which application is incorporated herein by reference in their entirety.

This application further incorporates herein by reference in entirety the following:

International Application (PCT) No. PCT/IB2006/051567, entitled METHODS FOR FABRICATING MICRO-ELECTRO-MECHANICAL DEVICES, filed on May 18, 2006;

International Application (PCT) No. PCT/IB2006/051568, entitled MICRO-ELECTRO-MECHANICAL TRANSDUCERS, filed on May 18, 2006;

International Application (PCT) No. PCT/IB2006/051569, entitled MICRO-ELECTRO-MECHANICAL TRANSDUCERS, filed on May 18, 2006; and International Application (PCT), PCT/IB2006/052658, entitled MICRO-ELECTRO-MECHANICAL TRANSDUCER HAVING A SURFACE PLATE, filed on Aug. 3, 2006.

FIELD OF THE INVENTION

The present invention relates to micro-electro-mechanical devices that have a movable mechanical part to function as an acoustic filter, particularly to work with PZT transducers and micromachined ultrasonic transducers (MUT) such as capacitance micromachined ultrasonic transducers (cMUT).

BACKGROUND OF THE INVENTION

Acoustic filters play an important role in many acoustic applications. Ultrasonic filters are used to condition the ultrasonic signal to be more suitable for the applications of ultrasonic transducers such as PZT transducers and MUT transducers. For example, ultrasonic filters can be used to shape the frequency bandwidth of the transducer, introduce desired phase delay and serve as the matching layer or the backing layer of the transducer. Usually the conventional ultrasonic filters are made of one layer or multiple layers of materials with desired thickness and acoustic properties.

In ultrasound imaging applications (such as ultrasonic non-destructive tests and ultrasonic diagnosis), for example, proper filtering is essential to obtain a good range of resolution. Transducer sensitivity and bandwidth are generally improved by adding single or multiple quarter-wave length matching layers between the transducer and the load medium, and this in turn reduces losses between the transducer and load medium. A matching layer is a thin layer of material placed on the front surface of an ultrasound transducer to improve the transfer of ultrasound into the medium of propagation (e.g. soft tissue). The thickness of the layer is usually equal to one fourth the wavelength of the ultrasound in the matching layer (the so-called quarter-wave matching), and the acoustic impedance is often about the geometric mean of the impedances on each side of the matching layer for effective matching. Multiple matching layers have also been used because using multiple layers with decreasing impedance provides a more gradual transition from the high impedance of the element to the low impedance of the body. In addition to matching layers in the front of the transducer, acoustic backing materials are also used at the back of the transducer to block ultrasound leaking into the substrate.

Conventional acoustic filters having one or more material layers have been used with a variety of ultrasound transducers, including piezoelectric transducers (PZT) and micromachined ultrasonic transducers. An ultrasound transducer performs a chain of energy transformation to realize its function of a transducer. In its receiving mode, the acoustic energy of ultrasound waves propagating in a medium where the transducer is placed is transformed to mechanical energy of a movable part (conventionally a vibrating membrane) in the transducer. The motion of the movable part is then transformed to a detectable electromagnetic (usually electrical) signal. In its transmitter mode, the reverse chain of energy transformation takes place.

Various types of ultrasonic transducers have been developed for transmitting and receiving ultrasound waves. Ultrasonic transducers can operate in a variety of media including liquids, solids and gas. These transducers are commonly used for medical imaging for diagnostics and therapy, biochemical imaging, non-destructive evaluation of materials, sonar, communication, proximity sensors, gas flow measurements, in-situ process monitoring, acoustic microscopy, underwater sensing and imaging, and many others. In addition to discrete ultrasound transducers, ultrasound transducer arrays containing multiple transducers have been also developed. For example, two-dimensional arrays of ultrasound transducers are developed for imaging applications.

Compared to the widely used piezoelectric (PZT) ultrasound transducer, the MUT has advantages in device fabrication method, bandwidth and operation temperature. For example, making arrays of conventional PZT transducers involves dicing and connecting individual piezoelectric elements. This process is fraught with difficulties and high expenses, not to mention the large input impedance mismatch problem presented by such elements to transmit/receiving electronics. In comparison, the micromachining techniques used in fabricating MUTs are much more capable in making such arrays. In terms of performance, the MUT demonstrates a dynamic performance comparable to that of PZT transducers. For these reasons, the MUT is becoming an attractive alternative to the piezoelectric (PZT) ultrasound transducers.

Among the several types of MUTs, the capacitive micromachined ultrasonic transducer (cMUT), which uses electrostatic transducers, is widely used. Other MUTs using piezoelectric (pMUT) and magnetic (mMUT) transducers are also adopted.

In general, both matching layers and backing layers are needed for PZT transducer because the significant mismatch of the acoustic impedance between the PZT material and the medium. One of the major disadvantages of the PZT transducer is the narrow bandwidth. A matching layer and a backing layer are therefore usually needed to improve the bandwidth of a PZT. For cMUT, there is usually less need for such layers, especially the matching layer, because the cMUT have better impedance match with the medium and can often exchange energy with the medium without the match layer. However, even cMUT may still benefit from acoustic filtering designed for other purposes.

In the prior art, the matching layer and backing layer is usually a single or multiple layers of special materials with particular acoustic impedances and precise thicknesses. For multiple layers, different types of materials are often needed for different layers. Often, finding a material with exactly acoustic impedance and coating a layer to the exactly thickness can be a challenge for just a single layer, especially for a high frequency transducers, 2D transducer arrays or IVUS side-view transducers, and much more so for multiple layers of high order filtering.

SUMMARY OF THE INVENTION

This application discloses a MEMS acoustic filter having a MEMS resonator and at least two acoustic I/O ports to alter an input acoustic signal to an output acoustic signal. The first I/O port is adapted for interfacing with a medium, and the second I/O port for passing an acoustic signal to an acoustic transducer. The MEMS resonator may either be passive or active.

In some embodiments, the MEMS acoustic filter is bidirectional in which the input port and the output port are interchangeable.

In one embodiment, one I/O port of a MEMS acoustic filter may be attached to a micromachined ultrasonic transducer element to alter its acoustic signal. Another I/O port of a MEMS acoustic filter may interface with and deliver the altered acoustic signal to a medium.

In one embodiment, MEMS resonator is a first-order resonator. In another embodiment, the MEMS resonator is a higher-order resonator. The higher-order resonator may have a plurality of first-order resonators. The plurality of first-order resonators may be stacked on one another. In one embodiment, MEMS resonator comprises a first resonator and a second resonator, wherein the first resonator has a first I/O port adapted for being attached to an ultrasound transducer, and the second resonator has a second I/O port adapted for interfacing with a medium. The first resonator may have a third I/O port, and the second resonator may have a fourth I/O port, wherein the third I/O port and the fourth I/O port are directly or indirectly connected together.

In one embodiment, the MEMS resonator comprises a flexible membrane layer; a least one connector; and a base layer, wherein a bottom surface of the flexible membrane layer is connected to the base layer through the at least one connector. The flexible membrane layer may have a top surface adapted for serving as at least a part of the first I/O port, and the base layer may have a bottom surface adapted for serving as at least a part of the second I/O port. In one embodiment of an active MEMS acoustic filter, the flexible membrane layer comprises a first electrode and the base layer comprises a second electrode.

In another embodiment, the MEMS resonator comprises a mass layer; a spring layer; and a base layer, wherein the mass layer has a bottom surface connected to a top surface of the spring layer through a spring-mass connector, and the spring layer is connected to the base layer. In one embodiment, the spring layer has a bottom surface connected to a top surface of the base layer through a spring anchor. The mass layer may be connected to the spring layer through a plurality of spring-mass connectors, and the spring layer may be connected to the base layer through a plurality of spring anchors, the plurality of spring anchors being disposed in intervals of the plurality of spring-mass connectors. The mass layer may have a top surface adapted for serving as at least a part of the first acoustic I/O port, and the base layer has a bottom surface adapted for serving as at least a part of the second acoustic I/O port. This embodiment may also be an active MEMS acoustic filter in which one of the mass layer or spring comprises a first electrode and one of the spring and the base layer comprises a second electrode.

The MEMS acoustic filter may be used with a variety of acoustic transducers. In one embodiment, the MEMS acoustic filter is attached to a micromachined ultrasonic transducer (MUT) element. A bonding interface layer may be used for attachment. In all the embodiments, the MEMS acoustic filter may be attached to a capacitive micromachined ultrasonic transducer (cMUT) element, a piezoelectric micromachined ultrasonic transducer (pMUT) element, a magnetic micromachined ultrasonic transducer (mMUT) element, or a piezoelectric transducer (PZT).

Another aspect of the present invention is an ultrasonic transducer comprising an ultrasonic transducer element and a MEMS acoustic filter attached to the ultrasonic transducer element. The MEMS acoustic filter comprises a MEMS resonator. In one embodiment, the MEMS resonator comprises an anchor layer and a spring layer defining a cantilever anchored on the anchor layer. Multiple MEMS resonators may be attached to one ultrasonic transducer. The MEMS resonators may be stacked together. For example, the first MEMS resonator may be attached to a back end of the ultrasonic transducer element to connect to a substrate, and the second MEMS resonator may be attached to a front end of the ultrasonic transducer to interface with a medium. The MEMS resonator may be attached to the ultrasonic transducer element through a conductive layer.

One aspect of the present invention is a micromachined ultrasonic transducer array comprising an array of micromachined ultrasonic transducer elements; and an array of MEMS acoustic filters each attached to a respective micromachined ultrasonic transducer element. In one embodiment, the array of MEMS acoustic filters is each characterized by a phase factor, and at least two of MEMS acoustic filters have different phase factors. Furthermore, the array of MEMS acoustic filters may have a pattern of phase factors arranged such that the array of MEMS acoustic filters function as an acoustic lens assisting to focus an acoustic beam to form an acoustic image. In one embodiment, the micromachined ultrasonic transducer array is a two dimensional array of micromachined ultrasonic transducer elements and MEMS acoustic filters. Each MEMS acoustic filter may comprise a MEMS resonator.

Another aspect of the present invention is a method for fabricating a MEMS acoustic filter. The method comprises the steps of: (1) depositing and patterning a first sacrificial layer on a substrate; (2) depositing and patterning a first structure layer over the first sacrificial layer; (3) depositing and patterning a second sacrificial layer; (4) depositing and patterning a second structure layer over the second sacrificial layer; and (5) removing the first and the second sacrificial layers, such that the first structure layer forms an anchor layer, and the second structure layer forms the spring layer defining a cantilever anchored on the anchor layer. In one embodiment, the method further comprises depositing and patterning a third sacrificial layer; and depositing and patterning a third structure layer over the third sacrificial layer, such that the third structure layer forms a plate layer above the spring layer.

Another aspect of the present invention is a method for fabricating a micromachined ultrasonic transducer. The method comprises the steps of forming a MEMS resonator on a substrate; bonding a micromachined ultrasonic transducer element to the MEMS resonator; and removing the substrate from the MEMS resonator.

In one embodiment, the method further comprises forming a bonding layer on the MEMS resonator, wherein the micromachined ultrasonic transducer is bonded to the MEMS resonator through the bonding layer.

Yet another aspect of the fabrication method comprises forming a micromachined ultrasonic transducer element on a substrate, wherein the micromachined ultrasonic transducer element has a top surface plate; and forming a MEMS resonator on the top surface plate of the micromachined ultrasonic transducer element. In one embodiment, the step of forming the MEMS resonator on the top surface plate comprises depositing and patterning a first sacrificial layer; depositing and patterning a first structure layer over the first sacrificial layer; depositing and patterning a second sacrificial layer; depositing and patterning a second structure layer over the second sacrificial layer; and removing the first and the second sacrificial layers, such that the first structure layer forms an anchor layer, and the second structure layer forms the spring layer defining a cantilever anchored on the anchor layer.

The foregoing and other features and advantages will become more apparent from the following detailed description of several embodiments, which proceeds with reference to the accompanying figures.

BRIEF DESCRIPTION OF THE DRAWINGS

FIG. 11 shows an example of one-dimensional array of transducers having a phase profile in accordance of the present invention.

FIGS. 12A and 12B show an array of transducers having MEMS filter array having a two-dimensional phase factor profile.

FIGS. 14.1-14.11 show an exemplary fabrication process for making a micromachined ultrasonic transducer having a MEMS filter in accordance with the present invention.

FIGS. 15.1-15.3 show an exemplary cMUT with embedded springs being bonded with MEMS filters of the present invention.

FIGS. 16.1-16.9 show an exemplary process for fabricating a MEMS matching layer of the present invention directly on a MEMS transducer layer.

DETAILED DESCRIPTION

Figure 1:
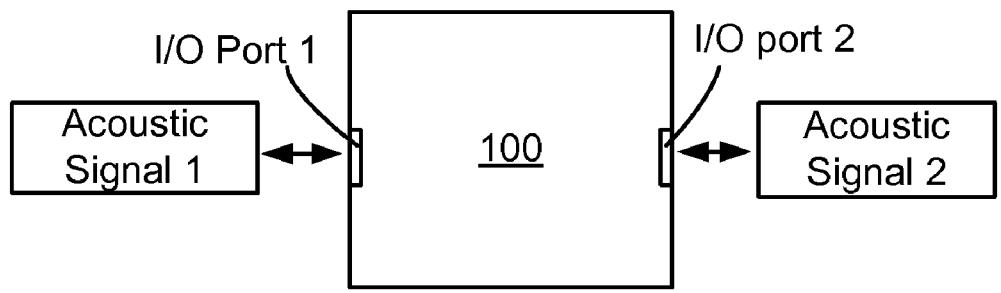
FIG. 1 shows a block diagram of a MEMS filter in accordance with the present invention.

The MEMS acoustic filter for altering an ultrasound signal in accordance with the present invention will be described in detail along with the figures, in which like parts are denoted with like reference numerals or letters. The MEMS acoustic filter may be used with a variety of acoustic transducers including PZT and micromachined ultrasonic transducers (MUT). The MEMS acoustic filter may be fabricated using the novel fabrication methods described herein, but may also be fabricated using any suitable methods. Particularly, some embodiments of the MEMS acoustic filter of the present invention may be fabricated using similar methods for making micromachined ultrasonic transducers, such as the methods disclosed in the several patent applications reference to and incorporated herein.

The invention has been described below with reference to specific embodiments. In most cases, a PZT transducer or cMUT structure is used to illustrate the invention. It is appreciated, however, that the present invention is not limited to PZT transducer and cMUTs. It will be apparent to those skilled in the art that various modifications may be made and other embodiments can be used without departing from the broader scope of the inventions. Therefore, these and other variations upon the specific embodiments are intended to be covered by the present inventions. Those skilled in the art will recognize that various features disclosed in connection with the embodiments may be used either individually or jointly.

It is noted that the terms "transducer" and "transducing member" are used in a broad sense in the present description to not only include devices that perform both actuation and sensing functions but also include devices that perform either an actuation function or an sensing function. It is also noted that the term "cantilever" is used in this description in a broad sense to describe a structure that has an anchored end, a resilient portion extending from the anchored, and to an exerting end to activate or move the resilient portion. A cantilever thus does not necessarily suggest a literal one-dimensional bema-like cantilever, but also includes similar structures have multibeams extending in different directions such as a bridge, or a crossbar, and most definitely also includes area or plane springs (two-dimensional "cantilevers") in which the anchored end is an extended line which may be a closed perimeter of an area or a portion thereof, the resilient portion is an extended area, and the exerting end may be a single point, a small area, or an extended line (close ended, open-ended, or segmented). In addition, the words "circular" and "annular" only suggest in the broadest sense that a shape has a looped form, a curved shape that is nearly looped, or an arrangement that is generally shaped like a ring, and do not suggest a rounded shape or any other shape in particular, nor does it suggest that the loop or ring is entirely complete or unbroken.

In this document, a conductive material is defined as one having a resistivity less than $1 \times 10^4$ $\Omega$-cm. Silicon and polysilicon materials are therefore considered conductive materials in this context. A good conductive material preferably has a resistivity less than 1 $\Omega$-cm. The terms "insulation material", "insulating material" and "dielectric material" are used interchangeably unless noted otherwise, and are defined as one having a resistivity greater than $1\times10^4\Omega$-cm. A good insulation/insulating material preferably has a resistivity greater than $1\times10^8\Omega$-cm. An insulator generally comprises an insulating material but in special cases may include air and vacuum.

In this invention, MEMS acoustic filters are introduced. The MEMS acoustic filter is used to process an acoustic signal, such as an ultrasonic signal. The MEMS acoustic filter alters an input acoustic signal and delivers an altered output acoustic signal to another device.

There are two ways to make MEMS ultrasonic filter of the present invention. One method is to fabricate each physical layer of a single layer filter or a multi-layer filter using MEMS fabrication method such that each layer has acoustic impedance and thickness similar to its counterpart in the conventional ultrasonic filter. In the conventional methods, there is a heavy burden to carefully choose a material having particular acoustic properties and to make the material into a layer with a very precise thickness. Very often, different materials must be chosen for multiple layer filters, further increasing the level of difficulty in selecting proper materials. Using MEMS technology, a material of approximate properties may be chosen and layers of the same material may be patterned using MEMS fabrication technology into different shapes to achieve different acoustic (ultrasonic) properties. As a result, a multilayer MEMS filter in accordance with the present invention may be made of the same materials with different patterns and thicknesses.

The present invention also introduces a unique method to make MEMS ultrasonic filters. This method makes a MEMS ultrasonic filter from one or multiple MEMS resonators. In other words, the present invention proposes using a MEMS resonator to replace a material layer of the conventional acoustic filter. Instead of selecting from existing materials for an ideal candidate having particular acoustic properties and make it into a layer of precise thickness, the present invention attains desired acoustic properties (particularly the frequency response) of each MEMS resonator by designing and engineering the MEMS resonator using MEMS technology. This approach results in a great deal of design freedom and engineering freedom. The frequency response of each MEMS resonator defines the phase and the amplitude of the response of the MEMS resonator to an input acoustic signal. The frequency response of a particular MEMS resonator is determined not only by the properties of the materials used but also by the mechanical and electrical design of the resonator.

For a single mass single spring resonator system, for example, usually two factors define the frequency response of the system. One is the resonant frequency and the other is the Q-factor. In such a resonator system, its phase factor is determined by the frequency difference between the input signal and the resonant frequency, as well as Q-factor. Careful designs of the resonant frequency and Q-factor of the resonator can therefore attain a desired acoustic property of a MEMS resonator which can serve as an equivalent of a "filter layer" in the conventional acoustic filter and to substitute it. For example, both matching layers and backing layers of a PZT transducer may be made MEMS ultrasonic filters with desired properties.

FIG. 1 shows a schematic block diagram of a MEMS filter in accordance with the present invention. A MEMS filter comprises a MEMS resonant structure 100 and at least two input/output (I/O), ports I/O Port 1 and I/O Port 2. In some embodiments, I/O ports may be interchangeable. For example, an input port may also be used as an output port, and vice versa. In operation, one I/O port receives an acoustic signal (Acoustic Signal 1) from a signal source (e.g., a medium) and the other I/O port delivers the altered acoustic signal (Acoustic Signal 2) to the next signal sink, such as an additional MEMS filter or an ultrasonic transducer.

Figure 2A:
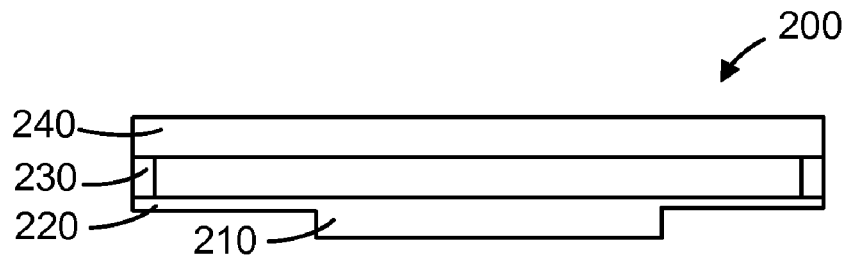
FIG. 2A shows a first exemplary MEMS acoustic filter in accordance with the present invention.

FIG. 2A shows a first exemplary MEMS acoustic filter in accordance with the present invention. The MEMS acoustic filter 200 has a mass layer 240; a spring layer 220; and a base layer 210. The mass layer 240 has a bottom surface connected to a top surface of the spring layer 220 through a spring-mass connector 230, and the spring layer 220 is connected to the base layer 210 to form a cantilever. The spring layer 220 and the base layer 210 may either be two separate layers or two integral portions of the same layer.

Figure 2B:
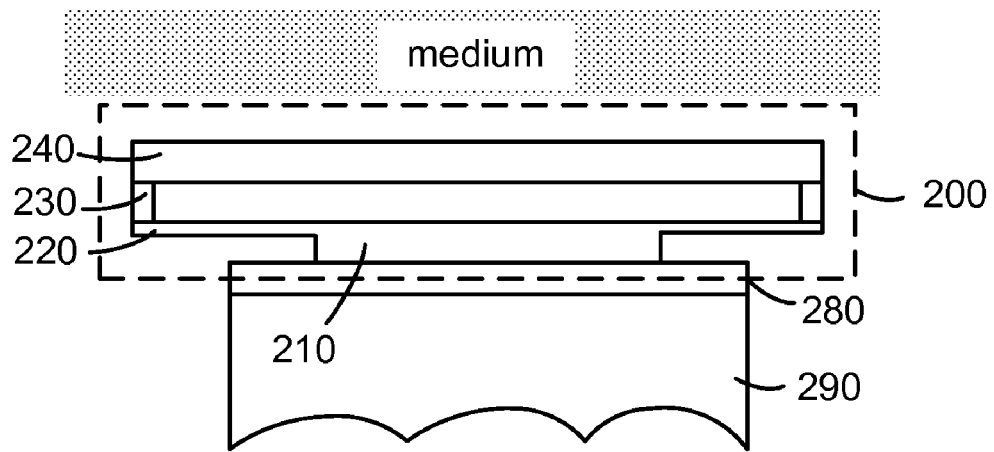
FIG. 2B shows the first exemplary MEMS acoustic filter in accordance with the present invention being used with an acoustic device.

FIG. 2B shows the first exemplary MEMS acoustic filter in accordance with the present invention being used with an acoustic device. In this embodiment, the base layer 210 is adapted to serve as one of the I/O port to be attached to an acoustic device 290, which may be a PZT transducer or MUT transducer or any other suitable acoustic device or an object having an acoustic property. The mass layer 240 is adapted to serve as another I/O port to interface with a medium. The MEMS acoustic filter 200 is attached to the acoustic device 290 through an attachment layer 280.

The MEMS acoustic filter 200 (collectively included in a box of dashed lines) interfaces with the medium for transducing purposes (such as sensing and actuation, or receiving and transmission).

From a purely mechanical point of view, the basic structure of the exemplary MEMS resonator 200 is therefore similar to a micromachined ultrasonic transducer itself. MEMS resonators of the present invention thus may be built using the same or similar methods for fabricating the micromachined transducers. For example, wafer bonding methods and surface micromachined methods, or any combination thereof, disclosed in the several patent applications referenced to and incorporated herein may be used, with slight modifications if necessary, to fabricate the MEMS resonators of the present invention.

Like the micromachined transducer, the mechanical structure of a MEMS resonator used as an acoustic filter in accordance with the present invention may be determined or constrained by the desired operation frequency and frequency response. Therefore, the dimensions of a MEMS resonator as an acoustic filter may be the same as a MUT transducer if both operate in the same frequency range, which is the case in some embodiments of the present invention where the MEMS acoustic filter and the MUT transducer are used together for the same application. These two devices therefore have very similar dimensions in such embodiments.

However, the MEMS acoustic filter and the MUT transducer are implemented quite differently because of their different operation modes and different purposes served. A MUT transducer may be used for transmission or reception, and it transforms one kind of input energy to another kind of output energy. For example, in a transmission mode, the input energy for a MUT transducer is an electrical signal, while the output energy is an acoustic signal, and vice versa in a receiving node. In contrast, a MEMS acoustic filter itself does not change the form of energy. Instead, it only alters (changing the amplitude or phase, or both, for example) a signal passing through the filter. Both input signal and output signal are the same kind, namely acoustic signals in accordance with the present invention. For this reason, the MEMS acoustic filter requires, at least, two acoustic I/O ports, one as an input port, another an output port.

The MEMS acoustic filter is usually located between two components in a system. In the particular example shown in FIG. 2B, the MEMS acoustic filter 200 is positioned between one the medium and the acoustic device 290 (e.g., a transducer).

Aside from the basic structure similarity, MEMS resonators of the present invention are generally built with design and performance considerations different from that of a transducer. The functional difference between the MEMS acoustic filter and the MUT transducer may lead to structural differences in details. For example, because the MEMS resonator is used as an ultrasonic filter in accordance with the present invention, it serves a different purpose than the micromachined ultrasonic transducer itself, and therefore generally has different designing parameters, such as frequency responses, as will be discussed further below. For another example, the substrate (base layer 210 in FIGS. 2A and 2B) of the MEMS acoustic filter 200 is desirably thin so that it will not add excessive mass loading on the transducer 290. In comparison, the substrate of a MUT transducer is usually much thicker, although it may also be made quite thin for some particular application (e.g. flexible CMUT).

A MEMS mechanical resonator may be designed to provide a filter function equivalent to a matching layer in the prior art. In particular, the filtering function of the most common and simple quarter-wave matching layer is a one-way quarter-wave delay line with proper acoustic impedance, and an equivalent filtering function (frequency response) can be readily attained using the MEMS resonator. For example, the acoustic impedance of the MEMS resonator illustrated in FIGS. 1-2 may be expressed as $$j(\omega m - k/\omega) + b,$$

where $\omega$ is the angular frequency, m, k and b are the mass, spring constant and the damping factor of the resonator respectively. By choosing proper values for m, k and b, the MEMS resonator can have desired amplitude and phase factor of its acoustical impedance. The amplitude of the acoustical impedance of the MEMS resonator can thus be chosen or tuned to match the acoustic impedance needed for the matching layer, while the phase factor can be chosen or tuned to match the quarter-wave delay for the matching layer. Other MEMS resonators may have a more complicated spring model, but nonetheless offer the same type of design freedom to attain a desired frequency response.

Different MEMS resonators may have a different resonance frequency and a different Q-factor. The frequency response of a particular MEMS resonator will determine, or at least affect, its acoustic properties as an acoustic filter. Because a MEMS resonator has several additional designing parameters other than the material properties, there is more design room to attain desired acoustic properties of each "filter layer" as compared to that in the prior art.

Besides serving as a matching layer, the MEMS acoustic filter of the present invention may also improve the bandwidth of the ultrasonic transducer. The frequency response of the whole device (the combination of the MEMS acoustic filter 200 and the acoustic device 290 in FIG. 2B, for example) is the product of the frequency responses of the acoustic device (e.g., 290) and the MEMS filter (e.g., 200). The frequency response of the whole device can therefore be shaped into a desired band shape using a proper MEMS filter.

Figure 2C:
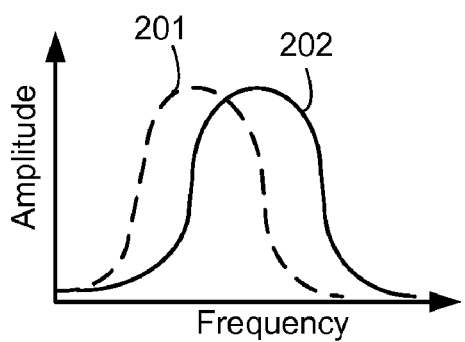
FIGS. 2C and 2D show an example of the frequency response of the whole transducer modified (shaped) by the frequency response of a MEMS acoustic filter.
Figure 2D:
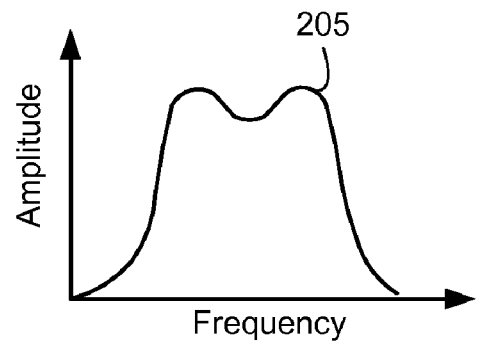

FIGS. 2C and 2D show an example of the frequency response of the whole transducer modified (shaped) by the frequency response of a MEMS acoustic filter. As shown in FIG. 2C, the MEMS acoustic filter has a frequency response 201, and the micromachined ultrasonic transducer element has a frequency response 202. As shown in FIG. 2D, the whole ultrasonic transducer (including both the transducer element and the MEMS filter) has a frequency response 205, which is different from the frequency response 202 of the ultrasonic transducer element without the MEMS ultrasonic filter.

As shown in FIG. 2D, when properly designed, even a first-order MEMS acoustic filter (a filter having a single MEMS filter) may widen the transducer bandwidth in the frequency domain.

Furthermore, a higher order MEMS filter may be used to further improve the performance of the MEMS matching layer. This is similar to conventional methods using multiple layers of desired materials to attain a better matching layer or a better filter function, but done using a high-order MEMS filter instead of stacking multiple layers of materials. More orders of the MEMS mechanical filter gives more orders of the freedoms to shape the frequency band of the MEMS filter so that it may result in a better overall bandwidth. A higher order MEMS acoustic filter can be built with multiple MEMS resonators as shown herein.

Based on the operating frequency requirement, alternative structures of MEMS acoustic filters may be preferred or even necessary. For some applications such as medical imaging applications, for example, it is envisioned that the following exemplary MEMS acoustic filters may be preferred.

Figure 3:
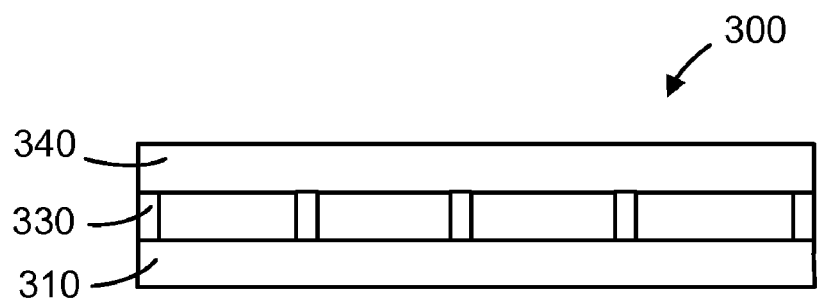
FIG. 3 shows a second exemplary MEMS acoustic filter in accordance with the present invention.

FIG. 3 shows a second exemplary MEMS acoustic filter in accordance with the present invention. The MEMS acoustic filter 300 has a base layer 310 and a flexible membrane layer 340 connected to the base 310 through multiple membrane anchors 330. The membrane layer may be clamped over the membrane anchors 330 in a way similar to a conventional membrane-based cMUT. The MEMS acoustic filter 300 may be attached to an acoustic device in the same way as shown in FIG. 2B. Specifically, the base layer 310 may be adapted to serve as one of the I/O port to be attached to an acoustic device, which may be a PZT transducer or MUT transducer, or any other suitable acoustic device or an object having an acoustic property. The flexible membrane layer 340 may be adapted to serve as another I/O port to interface with a medium. The MEMS acoustic filter 300 may be attached to the acoustic device through an attachment layer like the attachment layer 280 in FIG. 2.

Figure 4:
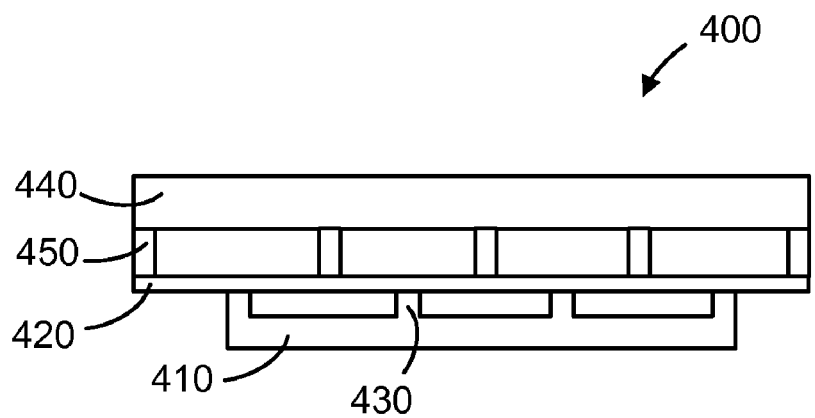
FIG. 4 shows a third exemplary MEMS acoustic filter in accordance with the present invention.

FIG. 4 shows a third exemplary MEMS acoustic filter in accordance with the present invention. The MEMS acoustic filter 400 has a base layer 410 and a spring layer 420 connected to the base layer 410 through multiple spring anchors 430. The MEMS acoustic filter 400 further has a mass layer 440 connected to the spring layer 420 through multiple spring-mass connectors 450. In the particular embodiment shown, the positions of the multiple spring anchors 430 and the positions of the multiple spring-mass connectors 450 are shifted from one another such that the former are generally positioned at the intervals of the latter. Unlike the flexible membrane 340 in FIG. 3, the mass layer 440 may either be flexible or very rigid compared with the spring layer 420. This design provides a distributed spring model and affords significant design freedom, similar to that of the embedded-spring micromachined ultrasonic transducers (ESMUT) as described in the several patent applications referenced to and incorporated herein.

The MEMS acoustic filter 400 may be attached to an acoustic device the same way shown in FIG. 2B. Specifically, the base layer 410 may be adapted to serve as one of the I/O port to be attached to an acoustic device. The mass layer 440 may be adapted to serve as another I/O port to interface with a medium. The MEMS acoustic filter 400 may also be attached to the acoustic device through an attachment layer like the attachment layer 280 in FIG. 2.

The MEMS acoustic filters shown in FIGS. 2-4 may be viewed as an equivalent of a single layer acoustic filter and to serve as a first-order acoustic filter. Multiple first-order acoustic filters may be stacked to form a multi-order acoustic filter as shown below.

Figure 5:
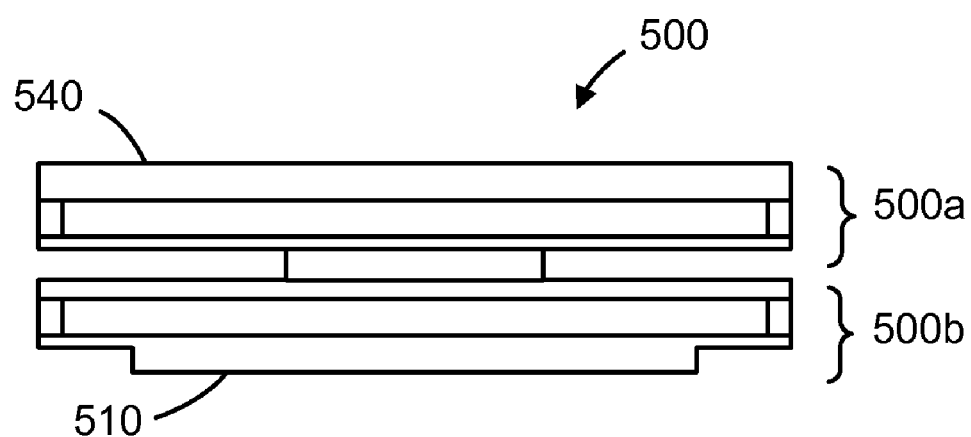
FIG. 5 shows a fourth exemplary MEMS acoustic filter in accordance with the present invention.

FIG. 5 shows a fourth exemplary MEMS acoustic filter in accordance with the present invention. The MEMS acoustic filter 500 is a two-order acoustic filter formed by stacking two first-order MEMS acoustic filters 500a and 500b, each of which has a similar structure to that of the MEMS acoustic filter 200 shown in FIG. 2A. The MEMS acoustic filter 500 has a base layer 510 and a spring layer 540, and may be attached to an acoustic device the same way as shown in FIG. 2B. Specifically, the base layer 510 may be adapted to serve as one of the I/O port to be attached to an acoustic device. The mass layer 540 may be adapted to serve as another I/O port to interface with a medium. The MEMS acoustic filter 500 may also be attached to the acoustic device through an attachment layer like the attachment layer 280 in FIG. 2. In the stacked configuration shown, the bottom of the top MEMS acoustic filter 500b is connected to the top of the bottom MEMS acoustic filter 500a. The former serves as an internal I/O port to send an interim output acoustic signal to the latter, which serves as another internal I/O port. In this manner, multiple first-order acoustic filters may be stacked to form a high order acoustic filter. The stacked acoustic filters 500a and 500b may use any type of MEMS acoustic filters of the present invention. The stacked acoustic filters 500a and 500b may have the same or a similar design, but may also have entirely different designs.

In addition to the MEMS resonators described above, MEMS resonators with any other design and structure may also be used as the MEMS acoustic filter in accordance with the present invention.

Figure 6:
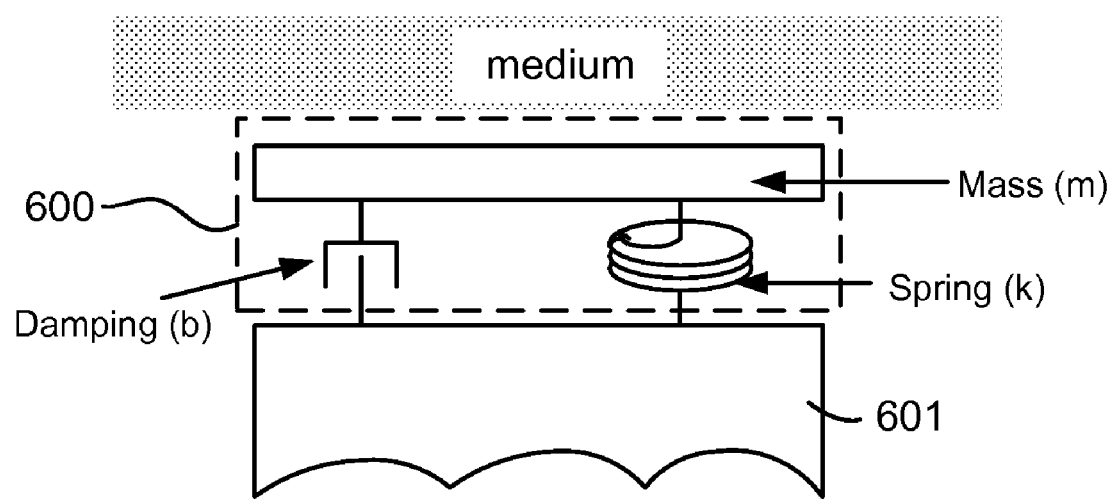
FIG. 6 shows a standard spring model that describes an equivalent of a MEMS resonator.

Like many other MEMS resonators, a first-order MEMS resonator can be described using a spring model. FIG. 6 shows a standard spring model that describes an equivalent of a MEMS resonator 600 similar to the MEMS resonator 200 shown in FIG. 2A. As shown, the spring model has a mass (m), a spring (k), and dashpot (b) for damping connected to the substrate 601.

Figure 7A:
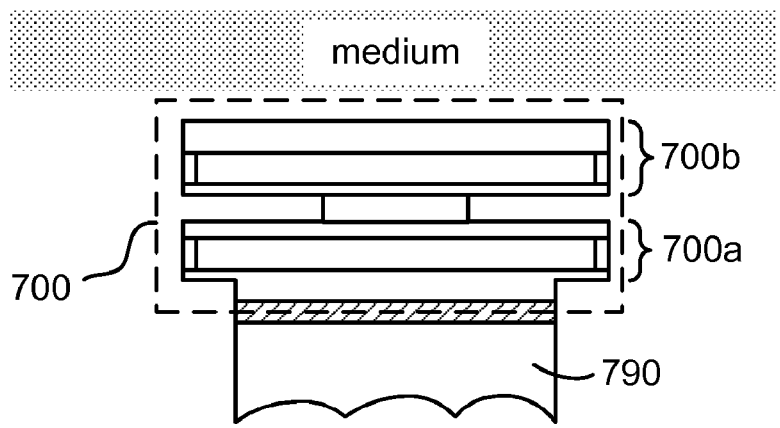
FIG. 7A shows an example of a second-order MEMS ultrasonic filter combined with an acoustic device.

FIG. 7A shows an example of a second-order MEMS ultrasonic filter combined with an acoustic device. The complete ultrasonic transducer has an ultrasonic transducer element 790 bonded to a second-order MEMS ultrasonic filter 700, which includes two MEMS resonators 700a and 700b, each of which is similar to the MEMS resonator 200 shown in FIGS. 2A-2B. Two MEMS resonators 700a and 700b shown in FIG. 7A can also be replaced by any other suitable MEMS resonator of the present invention, such as the MEMS resonator 300 in FIG. 3 or 400 in FIG. 4. Furthermore, the MEMS resonators 700a and 700b may be the same or different kinds of MEMS resonators.

Figure 7B:
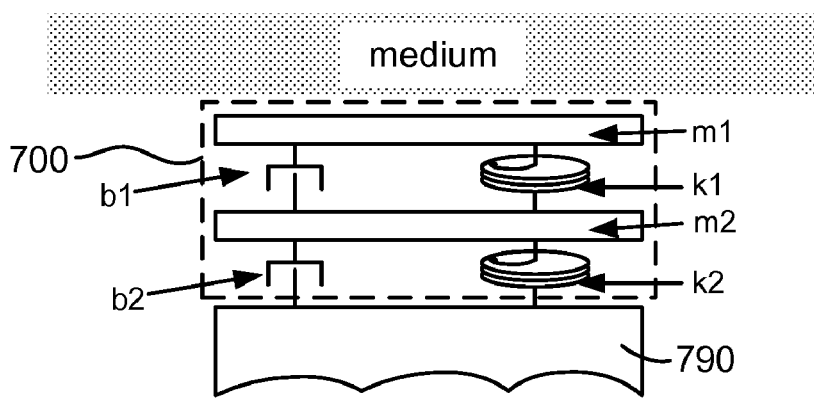
FIG. 7B shows a spring model that describes the equivalent of the second-order MEMS resonator shown in FIG. 7A.

FIG. 7B shows a spring model that describes the equivalent of the second-order MEMS resonator 700 shown in FIG. 7A. As shown, the spring model has two stacked springs with a first mass (m1), a first spring (k1), and first dashpot (b1) for damping; a second mass (m2), a second spring (k2), and a second dashpot (b2).

Figure 7C:
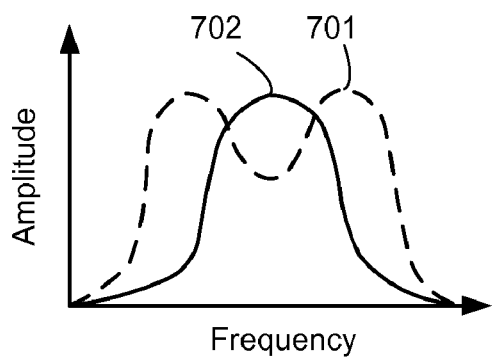
FIGS. 7C and 7D show an example of the frequency response of the whole transducer modified (shaped) by the frequency response of a second-order MEMS acoustic filter.
Figure 7D:
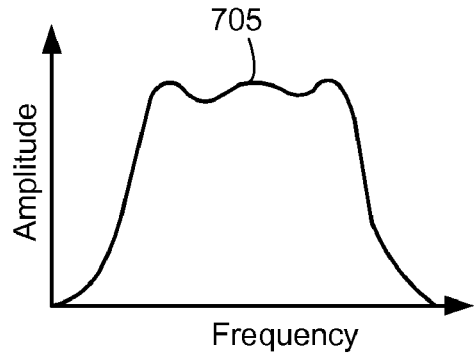

FIGS. 7C and 7D show an example of the frequency response of the whole transducer modified (shaped) by the frequency response of a second-order MEMS acoustic filter. As shown in FIG. 7C, the MEMS acoustic filter 700 has a frequency response 701, and the ultrasonic transducer element 790 has a frequency response 702. As shown in FIG. 7D, the whole ultrasonic transducer (including both the transducer element 790 and the MEMS acoustic filter 700) has a frequency response 705, which is different from the frequency response 702 of the ultrasonic transducer element 790 without the MEMS ultrasonic filter 700. Because a second-order MEMS acoustic filter has more design freedom than a first-order MEMS acoustic filter, it may be more effective in widening the transducer bandwidth in the frequency domain.

The MEMS acoustic filter in accordance with the present invention may also be supplied as a backing layer as shown below.

Figure 8A:
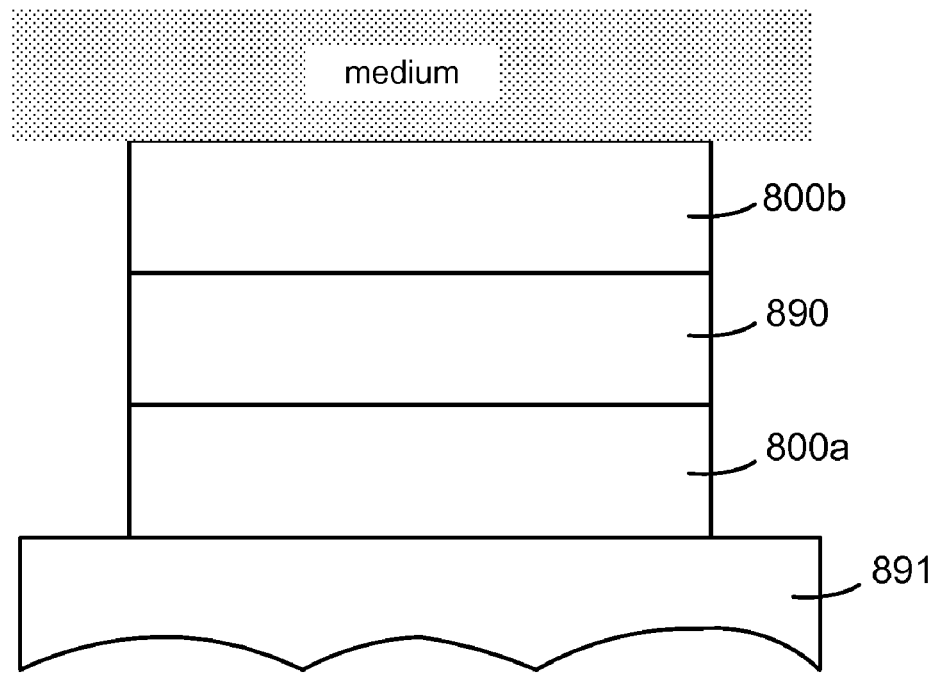
FIG. 8A shows an example of an ultrasonic transducer having both a MEMS matching filter and a MEMS backing filter.

FIG. 8A shows an example of an ultrasonic transducer having both a MEMS matching filter and a MEMS backing filter. The complete ultrasonic transducer has an ultrasonic transducer element 890 sandwiched between MEMS backing filter 800a and MEMS matching filter 800b. The matching filter 800b is placed between the transducer element 890 and the medium, while the backing filter 800a is placed between the transducer element 890 and a substrate 891.

Figure 8B:
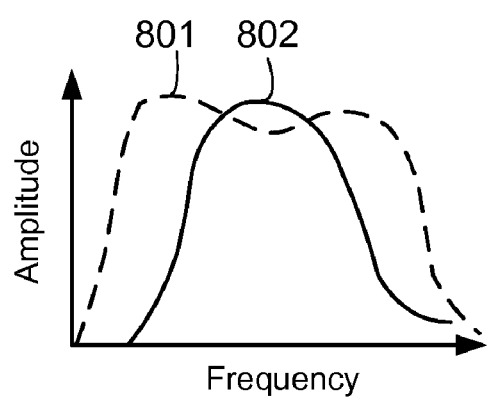
FIGS. 8B-8C show an example of the frequency response of a whole transducer modified (shaped) by the frequency response of a matching MEMS acoustic filter and a backing MEMS acoustic filter.
Figure 8C:
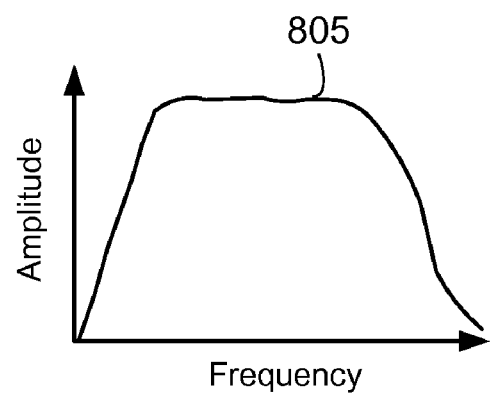

FIGS. 8B-8C show an example of the frequency response of a whole transducer modified (shaped) by the frequency response of a matching MEMS acoustic filter and a backing MEMS acoustic filter. The effect is similar to that of a second-order MEMS acoustic filter. As shown in FIG. 8B, the backing MEMS acoustic filter 800a and the matching MEMS acoustic filter 800b collectively have a frequency response 801, while the ultrasonic transducer 890 has a frequency response 802. As shown in FIG. 8C, the frequency response of the whole transducer 800 has a modified (broadened) frequency response 805.

Figure 9:
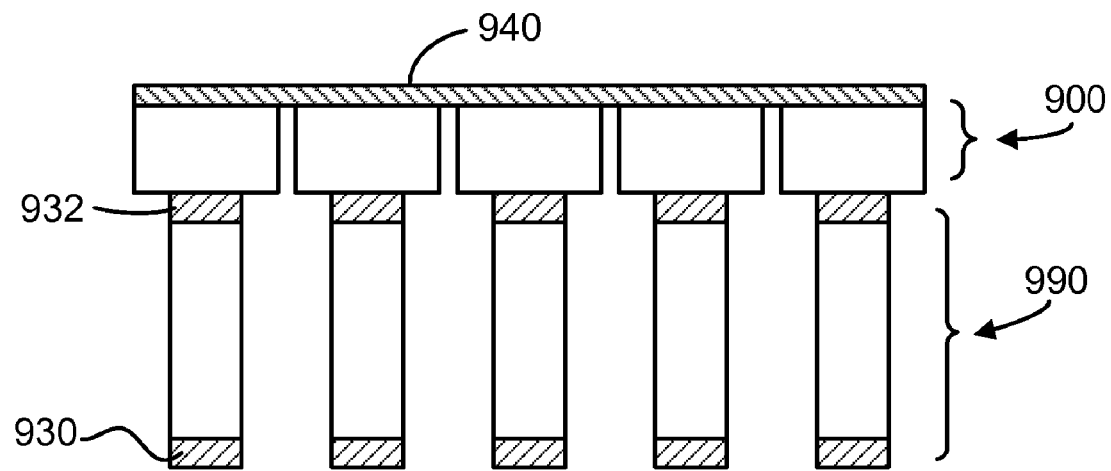
FIG. 9 shows an array of MEMS acoustic filters used on an array of PZT transducers in accordance with the present invention.

FIG. 9 shows an array of MEMS acoustic filters used on an array of PZT transducers in accordance with the present invention. An array of PZT transducers 990 are each bonded to a respective MEMS acoustic filter 900 through a contact layer 932, which may be an electrode. Another electrode 930 may also be included at the back end of each ultrasonic transducer 990. An array of PZT transducers is often used for ultrasonic imaging. For this type of applications, a lens layer 940 may also be used to assist focusing of the ultrasonic beam. Alternatively or additionally, the layer 940 may be a protection layer.

In addition to shaping the transducer bandwidth, the MEMS matching layer may also improve other performances of the PZT transducer. For example, due to the manufacture limitation, making a PZT transducer array with great uniformity is difficult, especially for a high frequency array or a 2-D array. Benefiting from the semiconductor process, the present invention may enhance the uniformity as shown below.

Figure 10:
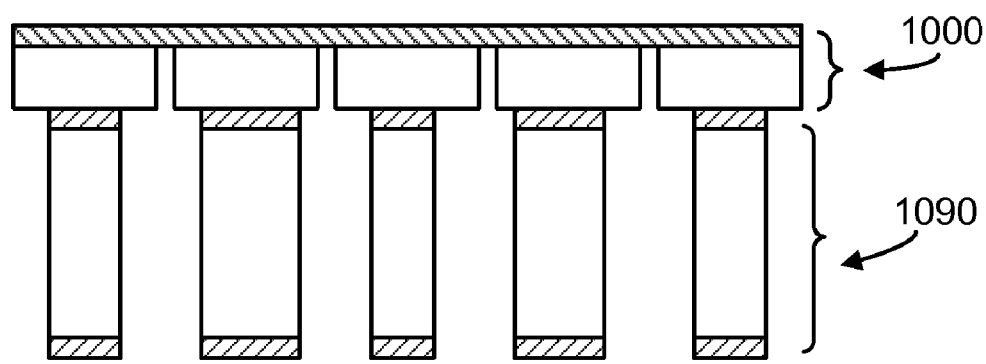
FIG. 10 shows an array of PZT transducers having nonuniform sizes and/or nonuniform locations, matched with an array of uniform MEMS matching layers of the present invention.

FIG. 10 shows an array of PZT transducers 1090 having non-uniform sizes and/or nonuniform locations, matched with an array of uniform MEMS matching layers of the present invention. Because the MEMS matching layer of the present invention for each transducer array element may be fabricated to be very uniform using semiconductor fabrication process, the overall uniformity of the transducer array is improved. Using MEMS matching layer in accordance with the present invention can therefore improve the performance uniformity of PZT transducer array.

The MEMS filter may also be used to change the phase of the ultrasonic signal. Because the amount of phase change may be controlled by using different MEMS filters having different acoustic properties, a particular phase change can be attained at a certain transducer element on the transducer array, and different phase changes may be assigned to different transducer elements. Using this method, a desired phase profile on an ultrasonic device or an array may be attained to achieve a desired acoustic function.

FIG. 11 shows an example of one-dimensional array of transducers having a phase profile in accordance of the present invention. The array of transducers includes transducer elements E1, E2, E3, E4, and E5, each connected to a respective MEMS filter F1, F2, F3, F4 and F5. The array of MEMS filters F1, F2, F3, F4 and F5 each has the characteristic phase factor. For example, MEMS filter F3 has a phase factor of "0", meaning that it does not change the phase of the ultrasonic signal passing through; MEMS filter F2 has a phase factor of "−α", meaning that it changes the phase of the ultrasonic signal passing through by an angle of "−α"; and so on.

Moreover, a MEMS filter associated with a certain transducer element may have multiple sub-filters positioned at different locations of the same transducer element to add different desired phase factors on the different locations. This method may be used to shape (condition) the ultrasonic beam to increase the imaging resolution and signal intensity at the center of the beam. An example is shown below.

FIGS. 12A and 12B show an array of transducers having MEMS filter array having a two-dimensional phase factor profile. As shown in FIG. 12A, an array of transducer elements E1, E2, E3, E4 and E5 is arranged along the X axis. An array of MEMS filters F1, F2, F3, F4, and F5 are attached to the array of transducer elements accordingly. From E1 to E5, a first dimension phase shift profile is generated by the array of MEMS filters F1-F5 such that transducer elements E1, E2, E3, E4 and E5 have phase shift profile of −2α, −α, 0, −α, and −2α, respectively. As shown in FIG. 12B, each MEMS filter (F1, F2, etc.) has sub-filters f1, f2, f3, f4 and f5, each positioned at different locations of each transducer element (E1, E2, etc.) along the Y axis. From f1 to f5, a second dimension phase shift profile is generated by the array of sub-filters f1-f5 such that five different locations of each transducer element along Y axis have phase shift profile of −2β, −β, 0, −β, and −2β, respectively. The phase shift angles α and β may be chosen according to the design need. For example, β may be 180°.

In one embodiment, a set of properly designed MEMS filters is used to add a desired phase factor on each element in a transducer array, such that the MEMS filters may be used as acoustic lens to shape the ultrasonic beam formation. An example is shown in FIG. 13.

Figure 13:
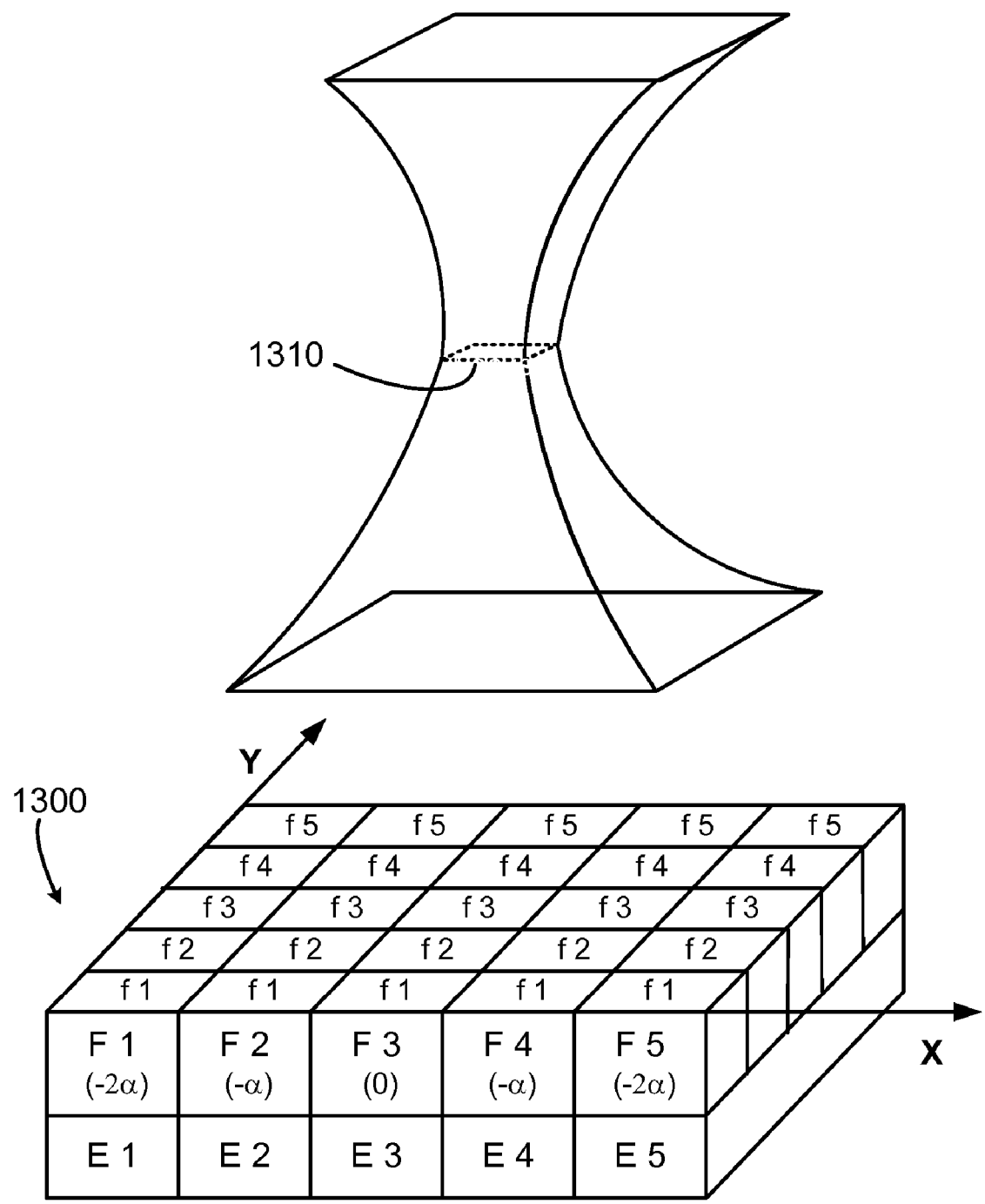
FIG. 13 shows a two-dimensional array of transducers with an array of MEMS filters and sub-filters capable to focus an ultrasonic beam passing the transducer.

FIG. 13 shows a two-dimensional array of transducers with an array of MEMS filters and sub-filters capable to focus an ultrasonic beam passing the transducer. As shown in FIG. 13, if the phase shift profile (the angles α and β and their arrangement) of the array of MEMS filters and sub-filters (including the) is carefully designed, the two-dimensional array of transducers 1300 may effectively focus the ultrasonic beam passing the transducer array 1300 such that the beam has a focal point at plan 1310.

Fundamentally, a lens is a device that changes the phase factor of the input wave at different locations. This is true for sound waves such as ultrasonic waves, as well as electromagnetic waves such as light. Phase change results in a change of the direction of wave propagation, such that the wave passing the lens is steered or focused at a desired location. All these required properties of an acoustic lens may be satisfied by designing a phase factor profile of a MEMS acoustic filter array.

Achieving focusing of an acoustic wave may require careful design of the phase factor profile. In the prior art, often choosing even a single proper filter layer can be a challenge, while choosing multiple layers can be much more difficult. It would be particularly difficult to choose an array of layers to attain a sophisticated phase shift profile or pattern to form a lens using the conventional ultrasonic filter layers. With the design freedom of MEMS acoustic filters of the present invention, this may be much more attainable.

The MEMS acoustic filters in accordance with the present invention can thus improve the imaging resolution and the signal intensity by focusing the ultrasound beam. This may be of critical importance for ultrasonic imaging. In a typical operation, an ultrasound imaging equipment focuses a single beam and obtains imaging information of the focus area one at a time. The equipment combines the information gathered at all focus areas and generates a full picture. The ability to focus a beam therefore is directly related to the resolution of the final image. The MEMS acoustic filter of the present invention has potential to improve these techniques.

The MEMS ultrasonic filter in accordance with the present invention may be used on a variety of ultrasonic transducers, including PZT transducers and micromachined ultrasonic transducers cMUT, pMUT and mMUT. As disclosed in the several patent applications referenced to and incorporated herein, cMUT, pMUT and mMUT may have the same or similar basic structures with the most essential difference being the transducing member included in the structure. Specifically, a cMUT has at least two electrodes as its transducing members; a pMUT has a piezoelectric member as its transducing member; while a mMUT has a magnetic member as its transducing member. The cMUT, pMUT and mMUT may be fabricated using any proper method including the methods disclosed in the several patent applications referenced to and incorporated herein.

MEMS filters built using MEMS resonators in accordance with the present invention may either be passive or active. A passive filter has no electrical power applied thereon directly. A passive filter may be a pure mechanical structure without any electrodes. The acoustic properties of a passive filter may be determined and fixed by the mechanical properties of the components in the filter. All parts of a passive filter can be made of either conductive or non-conductive materials. In an active filter, an electrical field may be applied on the filter to tune the properties of the filter. An active filter therefore generally has electrodes, and a DC bias is often used to tune the filter properties such as the spring strength of the mechanical structure. Compared to a passive MEMS filter, the structure of an active MEMS filter in accordance with the present invention may be even closer to that of a cMUT. For example, an active MEMS filter may use a cMUT structure with a very thin base layer.

Regardless of the difference, both the passive and active MEMS filters of the present invention may be attached to a transducer in the same manner, except that an active MEMS filter may need a DC bias voltage applied to tuning the filter.

Fabrication Methods:

A variety of MEMS resonators may be used. In particular, one embodiment a MEMS resonator of the present invention has a basic structure that is similar to that of the micromachined ultrasonic transducer itself. Both structures generally have an anchor layer and a spring layer defining a cantilever anchored on the anchor layer. A MEMS resonator may thus be based on any micromachined ultrasonic transducers disclosed in the several patent applications referenced and incorporated herein. Aside the fact that a MEMS resonator does not need a transducing member, the difference between a MEMS resonator and a micromachined ultrasonic transducer itself may lie in the actual frequency response only. Because a MEMS resonator is used for impedance matching, backing, transducer frequency response modification (such as broadening), a MEMS resonator may have a unique requirement for its frequency response different from that of the micromachined ultrasonic transducer.

The MEMS filters may be fabricated on a substrate then bonded on the cMUT or the PZT transducer using a proper bonding technology (e.g., eutectic bonding, thermal compression bonding, and various flip-chip bonding methods). The MEMS filter can also be built on the transducer directly by using a proper fabrication process.

Since the methods to build a MEMS filter as a matching layer and a MEMS filter as a backing layer are essentially the same or very similar, only the processes for fabricating MEMS filters as matching layers are described herein in detail. It is appreciated that these methods can also be used to build MEMS filters as backing layers for PZT transducers and various micromachined ultrasonic transducers such as cMUT, pMUT and mMUT.

Similar fabrication processes can be applied on a variety of transducers including PZT transducers and cMUTs. MEMS resonators may be fabricated on a silicon wafer using various technologies, such as wafer-bonding, surface micromachining or any combination of these technologies. In particular, because a MEMS resonator may have a basic mechanical structure similar to that of a MEMS transducer (except for not needing a transducing member such as an electrode or piezoelectric piece in a MEMS resonator for a passive MEMS acoustic filter), the processes for making micro-electro-mechanical (MEMS) transducers described in the several patent applications referenced to and incorporated herein may all be used for making a MEMS resonator of the present invention. Special design considerations, such as optimal frequency responses, however, should be given to MEMS resonators because they serve a different purpose than the MEMS transducer itself.

The MEMS resonator may be made from conductive or non-conductive material (e.g., silicon, polysilicon, silicon nitride, oxide, polyimide, polymer, metal, rubber, Teflon, Pryelene, PMMA, and PDMS). If fabricated separately, the MEMS resonator (either as a matching layer or backing layer) may be bonded to the transducer (PZT transducers, cMUT, etc.) using a proper bonding method such as eutectic bonding, thermal compression bonding, and flip-chip bonding.

FIGS. 14.1-14.11 show an exemplary fabrication process for making a micromachined ultrasonic transducer having a MEMS filter in accordance with the present invention. The steps of the process are described below.

In step one (FIG. 14.1), a sacrificial layer 1411 is deposited and patterned on substrate 1401. Subsequently, a structure layer 1420 is deposited over the sacrificial layer 1411.

In step two (FIG. 14.2), the structure layer 1420 is patterned, and a second sacrificial layer 1412 is deposited over the structure layer 1420. The patterned structure layer 1420 will become the mass layer (surface plate) of the final MEMS resonator.

In step three (FIG. 14.3), the second sacrificial layer 1412 is patterned and a second structure layer 1422 is deposited.

In step four (FIG. 14.4), the second structure layer 1422 is patterned. This will become the spring layer in the final MEMS resonator. At the same time, vias may be formed to facilitate sacrificial layer removal.

In step five (FIG. 14.5), a third sacrificial layer 1414 is deposited and patterned.

In step six (FIG. 14.6), a third structure layer 1424 is deposited. This completes the process for making a first-order MEMS filter. The above steps one through six can be repeated to fabricate a higher order MEMS filter if needed.

In step seven (FIG. 14.7), a bonding layer 1430 is deposited and patterned. The bonding layer 1430 may be a single layer or multiple layers of materials suitable for bonding.

In step eight (FIG. 14.8), the third structure layer 1424 is patterned to form individual MEMS resonators and also to prepare for separating the MEMS resonators from the substrate 1401.

In step nine (FIG. 14.9), the sacrificial layers 1411, 1412 and 1414 are removed.

In step ten (FIG. 14.10), transducers 1450 (such as a PZT transducer) are bounded to the MEMS resonators through bonding layer 1430.

In step eleven (FIG. 14.11), the MEMS resonators (collectively denoted as the MEMS matching layer 1440), together with the transducers 1450, is removed from the substrate 1401. After this, a protection layer (not shown), or another function layer such as an auxiliary lens layer, may be bonded on the top of the MEMS matching layer 1440 if needed to complete the transducer.

A variety of transducers, including cMUT, pMUT and mMUT, may be bonded to the MEMS matching layer 1440 fabricated using the process shown above. In particular, the micro-electro-mechanical (MEMS) transducers disclosed in the several patent applications referenced to and incorporated herein may all be used in combination with the present invention.

FIGS. 15.1-15.3 show an exemplary cMUT with embedded springs being bonded with MEMS filters of the present invention. The steps of the process are described below.

In step one (FIG. 15.1), the process starts with a MEMS matching layer 1440 which is the product of the step nine shown in FIG. 14.9 of the previous fabrication process. The MEMS matching layer 1440 has multiple MEMS resonators separated from one another by trenches 1445. Each MEMS resonator has a mass layer 1424 connected to a spring layer 1422 through a spring-mass connector 1425. The spring layer 1422 is connected to a base layer 1420 through spring anchors 1423 to form a membrane (plane) cantilever. The basic mechanical structure of the MEMS resonators show here is similar to that of the MEMS transducers described in the International Application (PCT), entitled MICRO-ELECTRO-MECHANICAL TRANSDUCER HAVING A SURFACE PLATE PCT/IB06/52658, filed on Aug. 3, 2006 by the common applicant, which patent application is fully incorporated herein by reference.

In step two, the MEMS matching layer 1440 is bonded to a MEMS transducer layer 1500 through a bonding layer 1430 using a proper bonding method (e.g., eutectic bonding, thermal compression bonding, and flip-chip bonding). The exemplary MEMS transducer layer 1500 has multiple MEMS transducer elements separated from one another by separation trenches 1555, which preferably are aligned with the separation trenches 1445 separating the individual MEMS resonators from one another if each MEMS transducer element is designed to be connected to one MEMS resonator.

Each MEMS transducer element has a base layer including substrate 1501 and spring anchor 1505, a spring layer 1520 connected to the substrate 1501 through a spring anchor 1505, a mass layer 1540 connected to the spring layer 1520 through spring-mass connectors 1530. A variety of MEMS transducer elements can be embodied using this basic mechanical structure, depending on the type of transducing member (electrodes, piezoelectric member or magnetic member) and on which layer the transducing member is built in the transducer structure. As described in the several patent applications referenced to and incorporated herein, in one embodiment each MEMS transducer element is a cMUT element having a bottom electrode on the spring layer 1520 or the substrate 1501 and a top electrode on the mass layer 1540. In another embodiment, each MEMS transducer element is a cMUT element having a bottom electrode on the substrate 1501 and a top electrode on the spring layer 1520.

In step three (FIG. 15.3), the MEMS matching layer 1440, together with the bonded MEMS transducer layer 1500, is released from the substrate 1401 to complete the fabrication process.

FIGS. 16.1-16.9 show an exemplary process for fabricating a MEMS matching layer of the present invention directly on a MEMS transducer layer. This integrated fabrication process is particularly suitable for adding a MEMS matching layer to a cMUT structure that has been fabricated using a similar or compatible process. The steps of the process are described below.

In step one (FIG. 16.1), the process starts with a MEMS transducer layer similar to the MEMS transducer layer 1500 described in FIG. 15.3. Each MEMS transducer element of the MEMS transducer layer has a base layer including substrate 1601 and spring anchor 1605, a spring layer 1620 connected to the substrate 1601 through a spring anchor 1605, a mass layer 1640 connected to the spring layer 1520 through spring-mass connectors 1630. The MEMS acoustic filter will be fabricated on top of the mass layer 1640. The process for fabricating MEMS resonators in the MEMS acoustic filter in this process is described in the following steps, and is similar but in a somewhat reversed order to the process described in FIGS. 14.1-14.9.

In step two (FIG. 16.2), a first sacrificial layer 1681 is deposited and patterned on the mass layer 1640 of the MEMS transducer layer.

In step three (FIG. 16.3), a first structure layer 1680 is deposited and patterned over the first sacrificial layer 1681. The first structure layer 1680 is to become the spring layer in the final MEMS resonator.

In step four (FIG. 16.4), a second sacrificial layer 1682 is deposited and patterned over the first structure layer 1680.

In step five (FIG. 16.5), a second structure layer 1660 is deposited over the second sacrificial layer 1682. The second structure layer 1660 is to become the mass layer in the final MEMS resonator. Vias for sacrificial etching may be opened if needed.

The above steps two through five may be repeated to form a high order MEMS filter.

In step six (FIG. 16.6), the sacrificial layers 1681 and 1682 are removed to form a gap between the spring layer 1680 and the surface plate (mass layer of the MEMS transducer) 1640, which serves as a base layer to the MEMS resonator. The spring layer 1680 is connected to the surface plate 1640 through anchors 1690. The removal of the sacrificial layers also forms a gap between the mass layer 1660 of the MEMS resonator and the spring layer 1680. The mass layer 1660 of the MEMS resonator is connected to the spring layer 1680 through spring-mass connectors 1670.

In step seven (FIG. 16.7), a metal layer 1665 is deposited and patterned over the mass layer 1660 two form a top electrode.

In step eight (FIG. 16.8), separation trenches 1675 are formed between MEMS transducer elements to separate the individual MEMS transducer elements.

In step nine (FIG. 16.9), a protection layer 1666 is coated or bonded to the top electrode 1665 if needed.

The fabrication methods shown above use surface micromachining methods. However, other methods such as wafer bonding processes described in the several patent applications referenced to and incorporated herein may also be used.

In the foregoing specification, the present disclosure is described with reference to specific embodiments thereof, but those skilled in the art will recognize that the present disclosure is not limited thereto. Various features and aspects of the above-described disclosure may be used individually or jointly. Further, the present disclosure can be utilized in any number of environments and applications beyond those described herein without departing from the broader spirit and scope of the specification. We claim all such modifications and variations that fall within the scope and spirit of the claims below. The specification and drawings are, accordingly, to be regarded as illustrative rather than restrictive. It will be recognized that the terms "comprising," "including," and "having," as used herein, are specifically intended to be read as open-ended terms of art.

The invention claimed is:

1. A MEMS acoustic filter comprising:
    a MEMS resonator; and
    at least two acoustic I/O ports.

2. The MEMS acoustic filter of claim 1 wherein the at least two acoustic I/O ports comprises a first I/O port adapted for interfacing with a medium, and a second I/O port adapter for interfacing with an acoustic transducer.

3. The MEMS acoustic filter of claim 1 wherein the MEMS resonator is passive.

4. The MEMS acoustic filter of claim 1 wherein the MEMS resonator is active.

5. The MEMS acoustic filter of claim 1 wherein the MEMS resonator is a first-order resonator.

6. The MEMS acoustic filter of claim 1 wherein the MEMS resonator is a higher-order resonator.

7. The MEMS acoustic filter of claim 1 wherein the MEMS resonator comprises a higher-order resonator having a plurality of first-order resonators.

8. The MEMS acoustic filter of claim 1 wherein the MEMS resonator comprises a higher-order resonator having a plurality of first-order resonators stacked on one another.

9. The MEMS acoustic filter of claim 1 wherein the MEMS resonator comprises a first resonator and a second resonator, the first resonator having a first I/O port adapted for being attached to an ultrasound transducer, and the second resonator having a second I/O port adapted for interfacing with a medium.

10. The MEMS acoustic filter of claim 9 wherein the first resonator having a third I/O port, and the second resonator having a fourth I/O port, the third I/O port and the fourth I/O port being directly or indirectly connected together.

11. The MEMS acoustic filter of claim 1 which is attached to a micromachined ultrasonic transducer (MUT) element.

12. The MEMS acoustic filter of claim 1 which is attached to a micromachined ultrasonic transducer (MUT) element through a bonding interface layer.

13. The MEMS acoustic filter of claim 1 which is attached to a capacitive micromachined ultrasonic transducer (cMUT) element.

14. The MEMS acoustic filter of claim 1 which is attached to a piezoelectric micromachined ultrasonic transducer (pMUT) element.

15. The MEMS acoustic filter of claim 1 which is attached to a magnetic micromachined ultrasonic transducer (mMUT) element.

16. The MEMS acoustic filter of claim 1 which is attached to a piezoelectric transducer (PZT).

17. An ultrasonic transducer comprising:
    an ultrasonic transducer element; and
    a MEMS acoustic filter attached to the ultrasonic transducer element.

18. The ultrasonic transducer of claim 17 wherein the MEMS acoustic filter comprises a MEMS resonator.

19. The ultrasonic transducer of claim 17 wherein the MEMS acoustic filter comprises a first MEMS resonator and a second MEMS resonator stacked together.

20. The ultrasonic transducer of claim 19 wherein the first MEMS resonator is attached to a back end of the ultrasonic transducer element to connect to a substrate, and the second MEMS resonator is attached to a front end of the ultrasonic transducer to interface with a medium.

21. The ultrasonic transducer of claim 17 wherein the ultrasonic transducer element comprises a capacitive transducing member.

22. The ultrasonic transducer of claim 17 wherein the ultrasonic transducer element comprises a piezoelectric transducing member.

23. The ultrasonic transducer of claim 17 wherein the MEMS acoustic filter comprises:
a MEMS resonator; and
at least two acoustic I/O ports.

24. An ultrasonic transducer array comprising:
an array of ultrasonic transducer elements; and
an array of MEMS acoustic filters each attached to a respective one of the array of ultrasonic transducer elements.

25. The ultrasonic transducer array of claim 24 wherein the array of MEMS acoustic filters is each characterized by a phase factor, at least two of the array of MEMS acoustic filters having different phase factors.

26. The ultrasonic transducer of claim 24 wherein the array of MEMS acoustic filters have a pattern of phase factors arranged such that the array of MEMS acoustic filters function as an acoustic lens assisting focusing an acoustic beam to form an acoustic image.

27. The ultrasonic transducer of claim 24 wherein the array of MEMS acoustic filters each comprises a MEMS resonator.

28. A MEMS acoustic filter comprising:
a MEMS resonator including a flexible membrane layer, a least one connector, and a base layer, wherein a bottom surface of the flexible membrane layer is connected to the base layer through the at least one connector; and
at least two acoustic I/O ports.

29. The MEMS acoustic filter of claim 28 wherein the at least two I/O ports comprise a first I/O port and a second I/O port, the flexible membrane layer has a top surface adapted for serving as at least a part of the first I/O port, and the base layer has a bottom surface adapted for serving as at least a part of the second I/O port.

30. The MEMS acoustic filter of claim 28 wherein the flexible membrane layer comprises a first electrode, and the base layer comprises a second electrode.

31. A MEMS acoustic filter comprising:
a MEMS resonator including a mass layer, a spring layer; and a base layer, wherein the mass layer has a bottom surface connected to a top surface of the spring layer through a spring-mass connector, and the spring membrane is connected to the base layer; and
at least two acoustic I/O ports.

32. The MEMS acoustic filter of claim 31 wherein the mass layer is connected to the spring layer through a plurality of spring-mass connectors, and the spring layer is connected to the base layer through a plurality of spring anchors, the plurality of spring anchors being disposed in intervals of the plurality of spring-mass connectors.

33. The MEMS acoustic filter of claim 31 wherein the at least two I/O ports comprise a first I/O port and a second I/O port, the mass layer has a top surface adapted for serving as at least a part of the first I/O port, and the base layer has a bottom surface adapted for serving as at least a part of the second I/O port.

34. The MEMS acoustic filter of claim 31 wherein one of the mass layer and spring layer comprises a first electrode, and one of the spring layer or the base layer comprises a second electrode.

* * * * *